(12) United States Patent
Dieken et al.

(10) Patent No.: US 11,324,950 B2
(45) Date of Patent: May 10, 2022

(54) ACCELEROMETER-BASED SENSING FOR SLEEP DISORDERED BREATHING (SDB) CARE

(71) Applicant: INSPIRE MEDICAL SYSTEMS, INC., Golden Valley, MN (US)

(72) Inventors: Dave Dieken, Golden Valley, MN (US); Kevin Verzal, Golden Valley, MN (US); John Rondoni, Golden Valley, MN (US); Quan Ni, Golden Valley, MN (US); Darrell Wagner, Golden Valley, MN (US); Christopher Thorp, Golden Valley, MN (US); Everardo Villasenor, Golden Valley, MN (US); Michael Hedin, Golden Valley, MN (US); Nicole C. Moskowitz, Golden Valley, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 0 days.

(21) Appl. No.: 16/092,384

(22) PCT Filed: Apr. 19, 2017

(86) PCT No.: PCT/US2017/028391
§ 371 (c)(1),
(2) Date: Oct. 9, 2018

(87) PCT Pub. No.: WO2017/184753
PCT Pub. Date: Oct. 26, 2017

(65) Prior Publication Data
US 2019/0160282 A1 May 30, 2019

Related U.S. Application Data

(60) Provisional application No. 62/324,388, filed on Apr. 19, 2016.

(51) Int. Cl.
*A61N 1/36* (2006.01)
*A61N 1/375* (2006.01)
(Continued)

(52) U.S. Cl.
CPC .......... *A61N 1/3601* (2013.01); *A61N 1/3611* (2013.01); *A61N 1/3752* (2013.01);
(Continued)

(58) Field of Classification Search
CPC .. A61N 1/3601; A61N 1/3611; A61N 1/3752; A61B 5/02405; A61B 5/0538;
(Continued)

(56) References Cited

U.S. PATENT DOCUMENTS 5,010,893 A  4/1991  Sholder
5,031,618 A  7/1991  Mullett
(Continued)

FOREIGN PATENT DOCUMENTS

CN  105769122 B  10/2018
CN  109259733 A  1/2019
(Continued)

OTHER PUBLICATIONS

Redmond et al., "Cardiorespiratory-Based Sleep Staging in Subjects With Obstructive Sleep Apnea," IEEE Transactions on Biomedical Engineering, vol. 53, No. 3, Mar. 2006, pp. 1-12.
(Continued)

*Primary Examiner* — Catherine M Voorhees
*Assistant Examiner* — Roland Dinga
(74) *Attorney, Agent, or Firm* — Dicke, Billig & Czaja, PLLC

(57) ABSTRACT

A first sensing element including an accelerometer-based sensor for sleep disordered breathing (SDB) care.

25 Claims, 13 Drawing Sheets

(51) Int. Cl.
  *A61B 5/024* (2006.01)
  *A61B 5/0538* (2021.01)
  *A61B 5/08* (2006.01)
  *A61B 5/11* (2006.01)
  *A61B 5/00* (2006.01)

(52) U.S. Cl.
  CPC ......... *A61B 5/02405* (2013.01); *A61B 5/0538* (2013.01); *A61B 5/0816* (2013.01); *A61B 5/1102* (2013.01); *A61B 5/1116* (2013.01); *A61B 5/4818* (2013.01); *A61B 2562/0219* (2013.01)

(58) Field of Classification Search
  CPC ... A61B 5/0816; A61B 5/1102; A61B 5/1116; A61B 5/4818; A61B 2562/0219
  See application file for complete search history.

(56) References Cited

U.S. PATENT DOCUMENTS

| | | |
|---|---|---|
| 5,233,984 A | 8/1993 | Thompson |
| 5,280,791 A | 1/1994 | Lavie |
| 5,342,409 A | 8/1994 | Mullett |
| 5,354,317 A | 10/1994 | Alt |
| 5,472,453 A | 12/1995 | Alt |
| 5,593,431 A | 1/1997 | Sheldon |
| 5,722,996 A | 3/1998 | Bonnet et al. |
| 5,732,696 A | 3/1998 | Rapoport et al. |
| 5,902,250 A | 5/1999 | Verrier et al. |
| 6,044,297 A | 3/2000 | Sheldon et al. |
| 6,064,910 A | 5/2000 | Andersson et al. |
| 6,161,041 A | 12/2000 | Stoop et al. |
| 6,466,821 B1 | 10/2002 | Pianca et al. |
| 6,641,542 B2 | 11/2003 | Cho et al. |
| 6,658,292 B2 | 12/2003 | Kroll et al. |
| 6,731,984 B2 | 5/2004 | Cho et al. |
| 6,748,272 B2 | 6/2004 | Carlson et al. |
| 6,773,404 B2 | 8/2004 | Poezevera et al. |
| 6,964,641 B2 | 11/2005 | Cho et al. |
| 7,025,729 B2 | 4/2006 | Chazal et al. |
| 7,117,036 B2 | 10/2006 | Florio |
| 7,123,954 B2 | 10/2006 | Narayan et al. |
| 7,155,278 B2 | 12/2006 | King et al. |
| 7,167,743 B2 | 1/2007 | Heruth et al. |
| 7,189,204 B2 | 3/2007 | Ni et al. |
| 7,252,640 B2 | 8/2007 | Ni et al. |
| 7,313,440 B2 | 12/2007 | Miesel et al. |
| 7,330,760 B2 | 2/2008 | Heruth et al. |
| 7,340,302 B1 | 3/2008 | Falkenberg et al. |
| 7,343,198 B2 | 3/2008 | Behbehani et al. |
| 7,366,572 B2 | 4/2008 | Heruth et al. |
| 7,371,220 B1 | 5/2008 | Koh et al. |
| 7,395,113 B2 | 7/2008 | Heruth et al. |
| 7,396,333 B2 | 7/2008 | Stahmann et al. |
| 7,435,221 B1 * | 10/2008 | Bharmi ............... A61B 5/02405 600/484 |
| 7,447,545 B2 | 11/2008 | Heruth et al. |
| 7,473,227 B2 | 1/2009 | Hsu et al. |
| 7,491,181 B2 | 2/2009 | Heruth et al. |
| 7,510,531 B2 | 3/2009 | Lee et al. |
| 7,530,956 B2 | 5/2009 | Lewicke et al. |
| 7,542,803 B2 | 6/2009 | Heruth et al. |
| 7,572,225 B2 | 8/2009 | Stahmann et al. |
| 7,578,793 B2 | 8/2009 | Todros et al. |
| 7,590,455 B2 | 9/2009 | Heruth et al. |
| 7,660,632 B2 | 2/2010 | Kirby et al. |
| 7,664,546 B2 | 2/2010 | Hartley et al. |
| 7,678,058 B2 | 3/2010 | Patangay et al. |
| 7,680,537 B2 | 3/2010 | Stahmann et al. |
| 7,717,848 B2 | 5/2010 | Heruth et al. |
| 7,757,690 B2 | 7/2010 | Stahmann et al. |
| 7,766,842 B2 | 8/2010 | Ni et al. |
| 7,775,993 B2 | 8/2010 | Heruth et al. |
| 7,792,583 B2 | 9/2010 | Miesel et al. |
| 7,853,322 B2 | 12/2010 | Bourget et al. |
| 7,862,515 B2 | 1/2011 | de Chazal et al. |
| 7,873,413 B2 | 1/2011 | McCabe et al. |
| 7,881,798 B2 | 2/2011 | Miesel et al. |
| 7,887,493 B2 | 2/2011 | Stahmann et al. |
| 7,896,813 B2 | 3/2011 | Sowelam et al. |
| 7,908,013 B2 | 3/2011 | Miesel et al. |
| 7,909,771 B2 | 3/2011 | Meyer et al. |
| 7,957,797 B2 | 6/2011 | Bourget et al. |
| 7,957,809 B2 | 6/2011 | Bourget et al. |
| 7,974,689 B2 | 7/2011 | Volpe et al. |
| 7,976,470 B2 | 7/2011 | Patangay et al. |
| 8,002,553 B2 | 8/2011 | Hatlestad et al. |
| 8,016,776 B2 | 9/2011 | Bourget et al. |
| 8,021,299 B2 | 9/2011 | Miesel et al. |
| 8,024,044 B2 | 9/2011 | Kirby et al. |
| 8,083,682 B2 | 12/2011 | Dalal et al. |
| 8,150,531 B2 | 4/2012 | Skelton |
| 8,175,720 B2 | 5/2012 | Skelton et al. |
| 8,192,376 B2 | 6/2012 | Lovett et al. |
| 8,209,028 B2 | 6/2012 | Skelton et al. |
| 8,231,555 B2 | 7/2012 | Skelton et al. |
| 8,231,556 B2 | 7/2012 | Skelton et al. |
| 8,265,759 B2 | 9/2012 | Tehrani et al. |
| 8,282,580 B2 | 10/2012 | Skelton et al. |
| 8,285,373 B2 | 10/2012 | Ternes et al. |
| 8,323,204 B2 | 12/2012 | Stahmann et al. |
| 8,323,218 B2 | 12/2012 | Davis et al. |
| 8,337,431 B2 | 12/2012 | Heruth et al. |
| 8,360,983 B2 | 1/2013 | Patangay et al. |
| 8,475,388 B2 | 7/2013 | Ni et al. |
| 8,535,222 B2 | 9/2013 | Ni et al. |
| 8,548,770 B2 | 10/2013 | Yuen et al. |
| 8,626,281 B2 | 1/2014 | Ternes et al. |
| 8,679,030 B2 | 3/2014 | Shinar et al. |
| 8,688,190 B2 | 4/2014 | Libbus et al. |
| 8,696,589 B2 | 4/2014 | Kwok et al. |
| 8,738,126 B2 | 5/2014 | Craig |
| 8,758,242 B2 | 6/2014 | Miesel et al. |
| 8,801,624 B2 | 8/2014 | Patangay et al. |
| 8,803,682 B2 | 8/2014 | Wong et al. |
| 8,836,516 B2 | 9/2014 | Wolfe et al. |
| 8,838,245 B2 | 9/2014 | Lin et al. |
| 8,862,226 B2 | 10/2014 | Ternes et al. |
| 8,870,764 B2 | 10/2014 | Rubin |
| 8,892,205 B2 | 11/2014 | Miller, III et al. |
| 8,905,948 B2 | 12/2014 | Davis et al. |
| 8,909,329 B2 | 12/2014 | Prakash et al. |
| 8,915,741 B2 | 12/2014 | Hatlestad et al. |
| 8,934,970 B2 | 1/2015 | Ternes et al. |
| 8,956,295 B2 | 2/2015 | Ni et al. |
| 8,961,413 B2 | 2/2015 | Teller et al. |
| 8,972,197 B2 | 3/2015 | Jangle et al. |
| 8,992,436 B2 | 3/2015 | Pu et al. |
| 9,026,223 B2 | 5/2015 | Skelton et al. |
| 9,031,650 B2 | 5/2015 | McCabe et al. |
| 9,056,195 B2 | 6/2015 | Sabesan |
| 9,060,880 B2 | 6/2015 | Van Beest |
| 9,159,223 B2 | 10/2015 | Proud |
| 9,204,798 B2 | 12/2015 | Proud |
| 9,218,574 B2 | 12/2015 | Phillipps et al. |
| 9,302,109 B2 | 4/2016 | Sabesan |
| 9,320,434 B2 | 4/2016 | Proud |
| 9,320,435 B2 | 4/2016 | Proud |
| 9,327,070 B2 | 5/2016 | Skelton et al. |
| 9,339,188 B2 | 5/2016 | Proud |
| 9,345,404 B2 | 5/2016 | Proud |
| 9,380,941 B2 | 7/2016 | Proud |
| 9,381,358 B2 | 7/2016 | Ternes et al. |
| 9,392,939 B2 | 7/2016 | Proud |
| 9,393,419 B2 | 7/2016 | Libbus et al. |
| 9,398,854 B2 | 7/2016 | Proud |
| 9,498,627 B2 | 11/2016 | Rosenberg et al. |
| 9,526,422 B2 | 12/2016 | Proud |
| 9,538,954 B2 | 1/2017 | Patangay et al. |
| 9,545,227 B2 | 1/2017 | Selvaraj et al. |
| 9,566,436 B2 | 2/2017 | Hoffer et al. |
| 9,582,748 B2 | 2/2017 | Proud et al. |
| 9,586,048 B2 | 3/2017 | Ternes et al. |

(56) References Cited

U.S. PATENT DOCUMENTS

| | | | |
|---|---|---|---|
| 9,610,030 B2 | 4/2017 | Proud | |
| 9,623,248 B2 | 4/2017 | Heruth et al. | |
| 9,655,559 B2 | 5/2017 | Chan et al. | |
| 9,656,082 B2 | 5/2017 | Denk | |
| 9,662,015 B2 | 5/2017 | Proud et al. | |
| 9,662,045 B2 | 5/2017 | Skelton et al. | |
| 9,675,268 B2 | 6/2017 | Bauer et al. | |
| 9,675,281 B2 | 6/2017 | Arnold et al. | |
| 9,681,838 B2 | 6/2017 | Halperin et al. | |
| 9,687,177 B2 | 6/2017 | Ramanan et al. | |
| 9,700,243 B2 | 7/2017 | Nakayama et al. | |
| 9,704,209 B2 | 7/2017 | Proud et al. | |
| 9,704,372 B2 | 7/2017 | Oorschot et al. | |
| 9,706,957 B2 | 7/2017 | Wu et al. | |
| 9,717,846 B2 | 8/2017 | Skelton et al. | |
| 9,731,126 B2 | 8/2017 | Ferree et al. | |
| 9,737,719 B2 | 8/2017 | Skelton et al. | |
| 9,743,848 B2 | 8/2017 | Breslow et al. | |
| 9,750,415 B2 | 9/2017 | Breslow et al. | |
| 9,763,767 B2 | 9/2017 | Abramson et al. | |
| 9,773,196 B2 | 9/2017 | Sachs et al. | |
| 9,814,429 B2 | 11/2017 | Lee et al. | |
| 9,821,165 B2 | 11/2017 | Gross | |
| 9,883,809 B2 | 2/2018 | Klap et al. | |
| 9,907,959 B2 | 3/2018 | Skelton et al. | |
| 9,919,159 B2 | 3/2018 | Skelton et al. | |
| 9,943,234 B2 | 4/2018 | Dalal et al. | |
| 9,974,959 B2 | 5/2018 | Moffitt et al. | |
| 9,987,488 B1 | 6/2018 | Gelfrand et al. | |
| 9,993,179 B2 | 6/2018 | Beest et al. | |
| 9,993,197 B2 | 6/2018 | Proud | |
| 9,999,351 B2 | 6/2018 | Proud | |
| 10,004,451 B1 | 6/2018 | Proud | |
| 10,010,253 B2 | 7/2018 | Eyal et al. | |
| 10,028,699 B2 | 7/2018 | Libbus et al. | |
| 10,071,197 B2 | 9/2018 | Skelton et al. | |
| 10,105,092 B2 | 10/2018 | Franceschetti et al. | |
| 10,159,421 B2 | 12/2018 | Heneghan | |
| 10,230,699 B2 | 3/2019 | Juels | |
| 10,300,230 B2 | 5/2019 | Flower et al. | |
| 10,357,163 B1 | 7/2019 | Selvaraj et al. | |
| 2003/0105497 A1 | 6/2003 | Zhu et al. | |
| 2005/0080349 A1 | 4/2005 | Okada et al. | |
| 2005/0085738 A1 | 4/2005 | Stahmann et al. | |
| 2005/0197588 A1 | 9/2005 | Freeberg | |
| 2005/0288728 A1 | 12/2005 | Libbus et al. | |
| 2006/0247729 A1 | 11/2006 | Tehrani et al. | |
| 2007/0032733 A1 | 2/2007 | Burton | |
| 2007/0115277 A1 | 5/2007 | Wang et al. | |
| 2007/0233194 A1 | 10/2007 | Craig | |
| 2007/0240723 A1 | 10/2007 | Hong et al. | |
| 2008/0021504 A1 | 1/2008 | McCabe et al. | |
| 2008/0033304 A1 | 2/2008 | Dalal et al. | |
| 2008/0051669 A1 | 2/2008 | Meyer et al. | |
| 2008/0234556 A1 | 9/2008 | Brooke et al. | |
| 2009/0062628 A1 | 3/2009 | Yamamoto et al. | |
| 2010/0010380 A1 | 1/2010 | Panken et al. | |
| 2010/0030085 A1 | 2/2010 | Ojeda et al. | |
| 2010/0094379 A1* | 4/2010 | Meadows | A61B 5/08 607/48 |
| 2010/0174335 A1 | 7/2010 | Stahmann et al. | |
| 2010/0286545 A1 | 11/2010 | Wolfe et al. | |
| 2011/0015702 A1 | 1/2011 | Ternes et al. | |
| 2011/0034811 A1 | 2/2011 | Naujokat et al. | |
| 2011/0046499 A1 | 2/2011 | Klewer et al. | |
| 2011/0060215 A1 | 3/2011 | Tupin, Jr. et al. | |
| 2011/0066041 A1 | 3/2011 | Pandia et al. | |
| 2011/0172744 A1 | 7/2011 | Davis et al. | |
| 2012/0179061 A1 | 7/2012 | Ramanan et al. | |
| 2012/0184825 A1 | 7/2012 | Ben David | |
| 2012/0192874 A1* | 8/2012 | Bolea | A61N 1/3601 128/848 |
| 2012/0290032 A1 | 11/2012 | Cho et al. | |
| 2013/0172769 A1 | 7/2013 | Arvind | |
| 2013/0245502 A1 | 9/2013 | Lange et al. | |
| 2013/0253616 A1 | 9/2013 | Libbus et al. | |
| 2014/0088373 A1 | 3/2014 | Phillips et al. | |
| 2014/0358825 A1 | 12/2014 | Phillipps et al. | |
| 2014/0364770 A1 | 12/2014 | Slonneger et al. | |
| 2014/0371817 A1 | 12/2014 | Mashiach et al. | |
| 2015/0073232 A1 | 3/2015 | Ahmad et al. | |
| 2015/0094962 A1 | 4/2015 | Hoegh et al. | |
| 2015/0164411 A1 | 6/2015 | Selvaraj et al. | |
| 2015/0173672 A1 | 6/2015 | Goldstein et al. | |
| 2015/0190089 A1* | 7/2015 | Christopherson | A61B 5/0809 600/301 |
| 2015/0224307 A1 | 8/2015 | Bolea et al. | |
| 2015/0238138 A1 | 8/2015 | Lehmann et al. | |
| 2015/0238304 A1 | 8/2015 | Lamraoui | |
| 2015/0238766 A1 | 8/2015 | McCabe et al. | |
| 2015/0273177 A1 | 10/2015 | Iizuka | |
| 2015/0283381 A1 | 10/2015 | Denk | |
| 2015/0283382 A1 | 10/2015 | Denk et al. | |
| 2015/0374279 A1 | 12/2015 | Takakura et al. | |
| 2016/0022204 A1 | 1/2016 | Mostov | |
| 2016/0029949 A1 | 2/2016 | Landesberg et al. | |
| 2016/0199215 A1 | 7/2016 | Kopelman | |
| 2016/0213309 A1 | 7/2016 | Sannholm et al. | |
| 2016/0256692 A1 | 9/2016 | Baru | |
| 2016/0310046 A1 | 10/2016 | Heinrich et al. | |
| 2016/0338648 A1 | 11/2016 | Faisal et al. | |
| 2016/0354602 A1 | 12/2016 | Keenan et al. | |
| 2016/0354603 A1 | 12/2016 | Hansen et al. | |
| 2016/0354608 A1 | 12/2016 | Keenan et al. | |
| 2016/0379041 A1 | 12/2016 | Rhee et al. | |
| 2017/0042471 A1 | 2/2017 | Meriheina | |
| 2017/0046563 A1 | 2/2017 | Kim et al. | |
| 2017/0056669 A1 | 3/2017 | Kane et al. | |
| 2017/0071533 A1 | 3/2017 | Warren et al. | |
| 2017/0076474 A1 | 3/2017 | Fu et al. | |
| 2017/0172459 A1 | 6/2017 | Bernstein et al. | |
| 2017/0172494 A1 | 6/2017 | Warren et al. | |
| 2017/0290528 A1 | 10/2017 | Ternes et al. | |
| 2017/0312515 A1 | 11/2017 | Ferree et al. | |
| 2017/0319109 A1 | 11/2017 | Skelton et al. | |
| 2018/0015282 A1 | 1/2018 | Waner et al. | |
| 2018/0064372 A1 | 3/2018 | Beest et al. | |
| 2018/0064388 A1 | 3/2018 | Heneghan et al. | |
| 2018/0078174 A1 | 3/2018 | Chan et al. | |
| 2018/0103895 A1 | 4/2018 | Yao | |
| 2018/0153476 A1 | 6/2018 | Annoni et al. | |
| 2018/0221660 A1 | 8/2018 | Suri et al. | |
| 2018/0344208 A1 | 12/2018 | Ogasawara et al. | |
| 2019/0076098 A1 | 3/2019 | Li et al. | |
| 2019/0099125 A1 | 4/2019 | Schnall | |
| 2019/0150772 A1 | 5/2019 | Haraikawa et al. | |
| 2019/0231257 A1 | 8/2019 | Javed | |
| 2019/0279363 A1 | 9/2019 | Steigauf et al. | |
| 2020/0107775 A1 | 4/2020 | de Chazal et al. | |

FOREIGN PATENT DOCUMENTS

| | | |
|---|---|---|
| EP | 1146433 A1 | 6/1985 |
| EP | 1711104 A1 | 10/2006 |
| EP | 2816968 B1 | 8/2018 |
| JP | 2009-532072 A | 9/2009 |
| JP | 2012-509155 A | 4/2012 |
| JP | 2012-533349 A | 12/2012 |
| KR | 20190081320 A | 7/2019 |
| WO | 2007/052108 A2 | 5/2007 |
| WO | 2010/059839 A2 | 5/2010 |
| WO | 2011/008747 A2 | 1/2011 |
| WO | 2016016469 A1 | 2/2016 |
| WO | 2016093927 A2 | 6/2016 |
| WO | 2017093054 A1 | 6/2017 |
| WO | 2017098609 A1 | 6/2017 |
| WO | 2017117335 A1 | 7/2017 |
| WO | 2017117636 A1 | 7/2017 |
| WO | 2017136352 A1 | 8/2017 |
| WO | 2017183039 A1 | 10/2017 |
| WO | 2017183602 A1 | 10/2017 |
| WO | 2017198787 A1 | 11/2017 |
| WO | 2017201419 A1 | 11/2017 |
| WO | 2017210055 A1 | 12/2017 |

(56) References Cited

FOREIGN PATENT DOCUMENTS

| WO | 2017211396 A1 | 12/2017 |
| WO | 2017223404 A1 | 12/2017 |
| WO | 2018006121 A1 | 1/2018 |
| WO | 2018016392 A1 | 1/2018 |
| WO | 2018068084 A1 | 4/2018 |
| WO | 2018081778 A1 | 5/2018 |
| WO | 2020132315 A1 | 6/2020 |
| WO | 2020169424 A1 | 8/2020 |

OTHER PUBLICATIONS

Stein et al., "Heart rate variability, sleep and sleep disorders," Sleep Medicine Reviews, vol. 16, Issue 1, Feb. 2012, pp. 47-66.
Girardin et al., "Sleep detection with an accelerometer actigraph: comparisons with polysomnography," Physiology & Behavior, vol. 72, Issue 1-2, Jan.-Feb. 2001, pp. 21-28.
PCT International Search Report and Written Opinion, Int'l Appl. No. PCT/US2020/043500, dated Oct. 26, 2020, pp. 1-14.
Invitation to Pay Additional Fees and, Where Applicable, Protest Fee (includes preliminary International Search Report), Int'l Appl. No. PCT/US2020/043442, dated Oct. 22, 2020, pp. 1-14.
"AASM clarifies hypopnea scoring criteria," American Academy of Sleep Medicine, Sep. 23, 2013, aasm.org/aasm-clarifies-hypopnea-scoring-criteria/.
Epstein et al., "Clinical Guideline for the Evaluation, Management and Long-term Care of Obstructive Sleep Apnea in Adults," Journal of Clinical Sleep Medicine, vol. 5, No. 3, 2009, pp. 263-276.
Immanuel et al., "Respiratory timing and variability during sleep in children with sleep-disordered breathing," J Appl Physiol 113, Sep. 27, 2012, pp. 1635-1642.
Morgenthaler et al., "Practice Parameters for the Medical Therapy of Obstructive Sleep Apnea," SLEEP, vol. 29, No. 8, 2006, pp. 1031-1035.
Phurrough et al., "Decision Memo for Continuous Positive Airway Pressure (CPAP) Therapy for Obstructive Sleep Apnea (OSA) (CAG-00093R2)," U.S. Centers for Medicare & Medicaid Services, Mar. 13, 2008, www.cms.gov/medicare-coverage-database/details/nca-decision-memo.aspx?NCA.
Rodriguez, Julia, "What do AHI, RERA, Arousal and RDI mean?," The Sleep Blog, Advanced Sleep Medicine Services, Inc., www.sleepdr.com/the-sleep-blog/what-do-ahi-rera-arousal-and-rdi-mean/ ResMed 2019.

\* cited by examiner

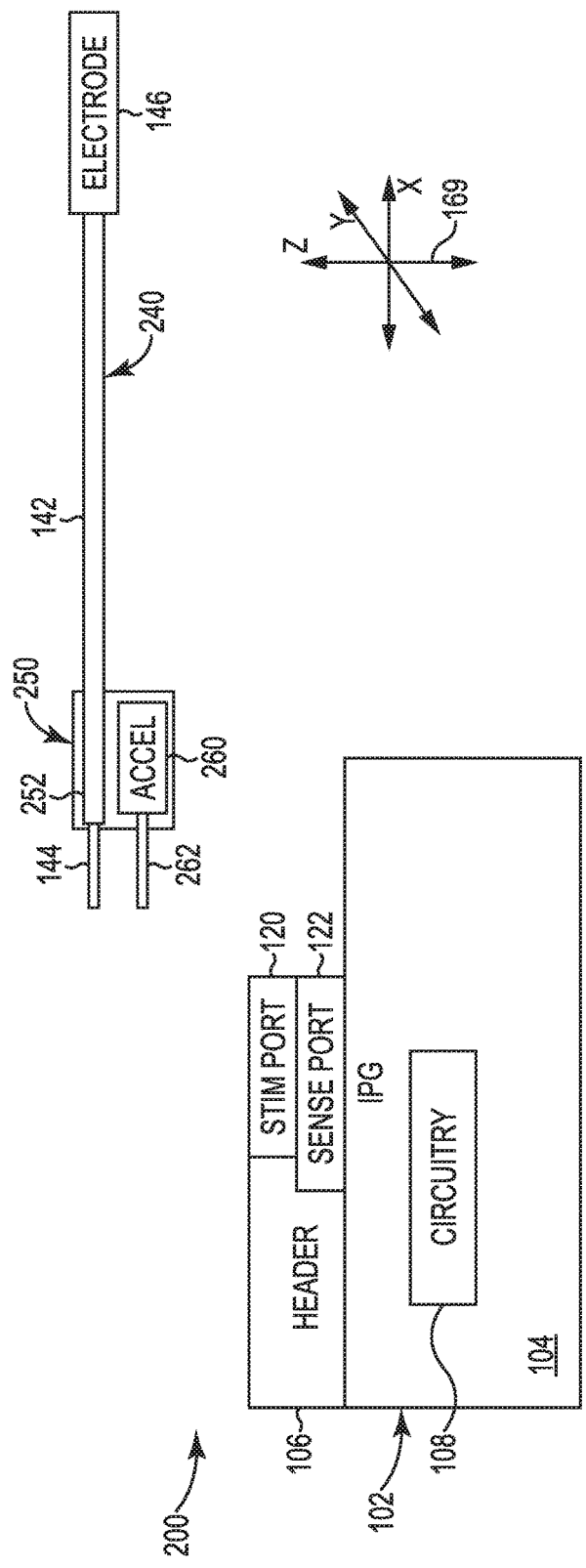
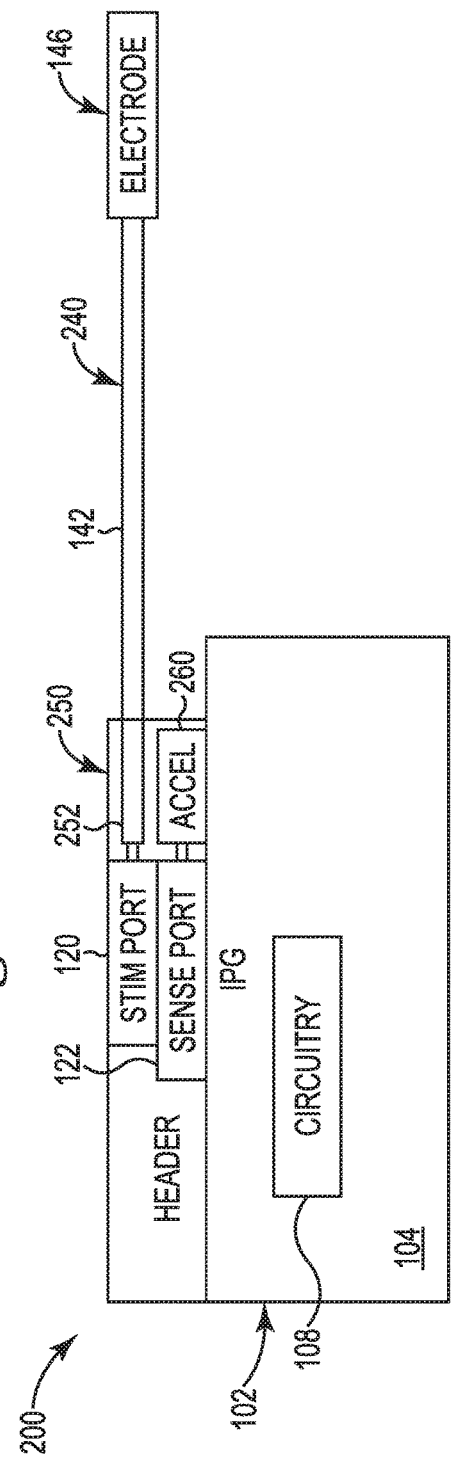

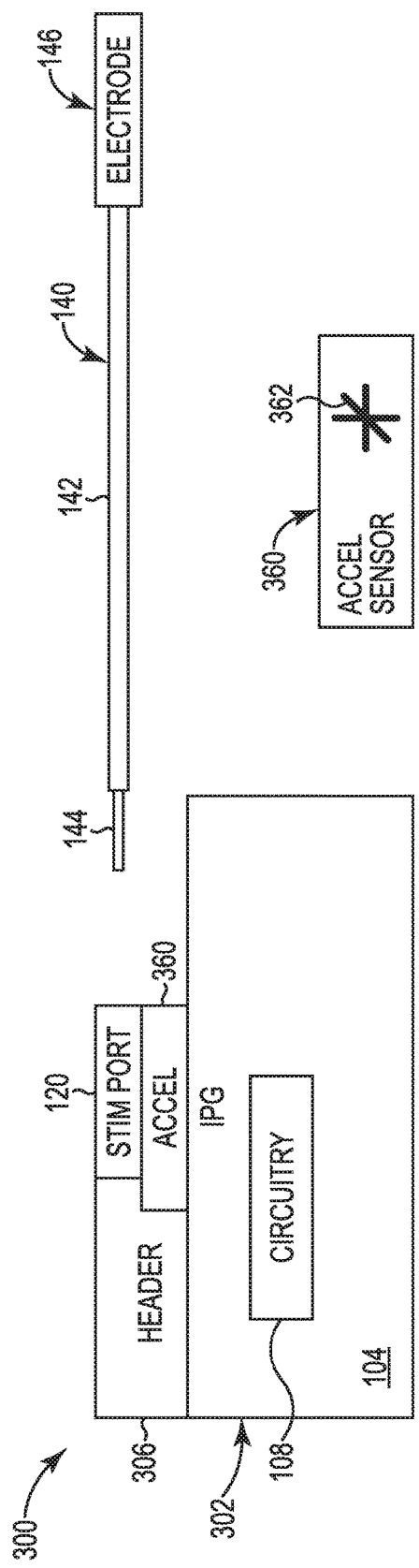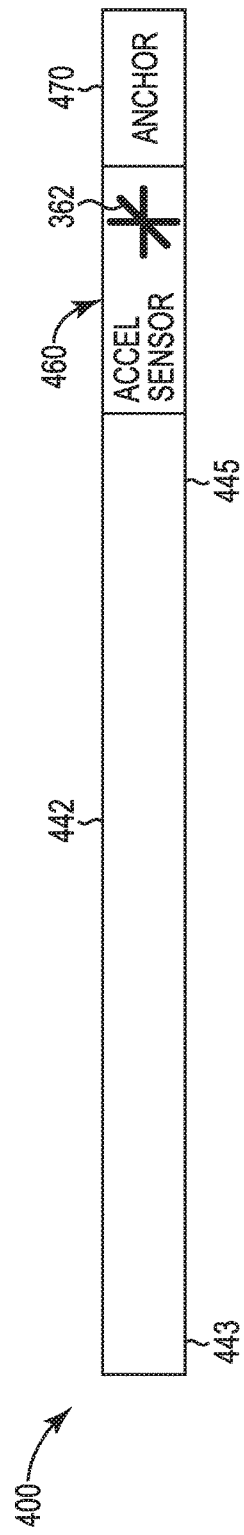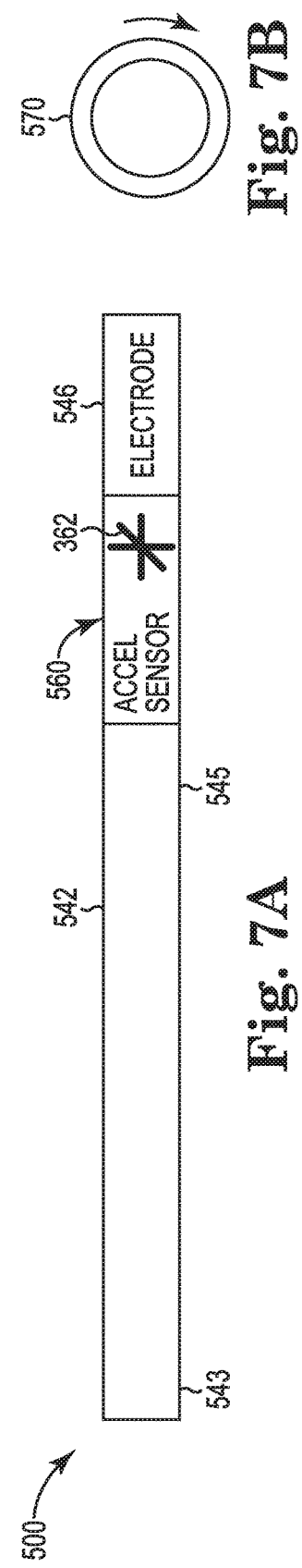

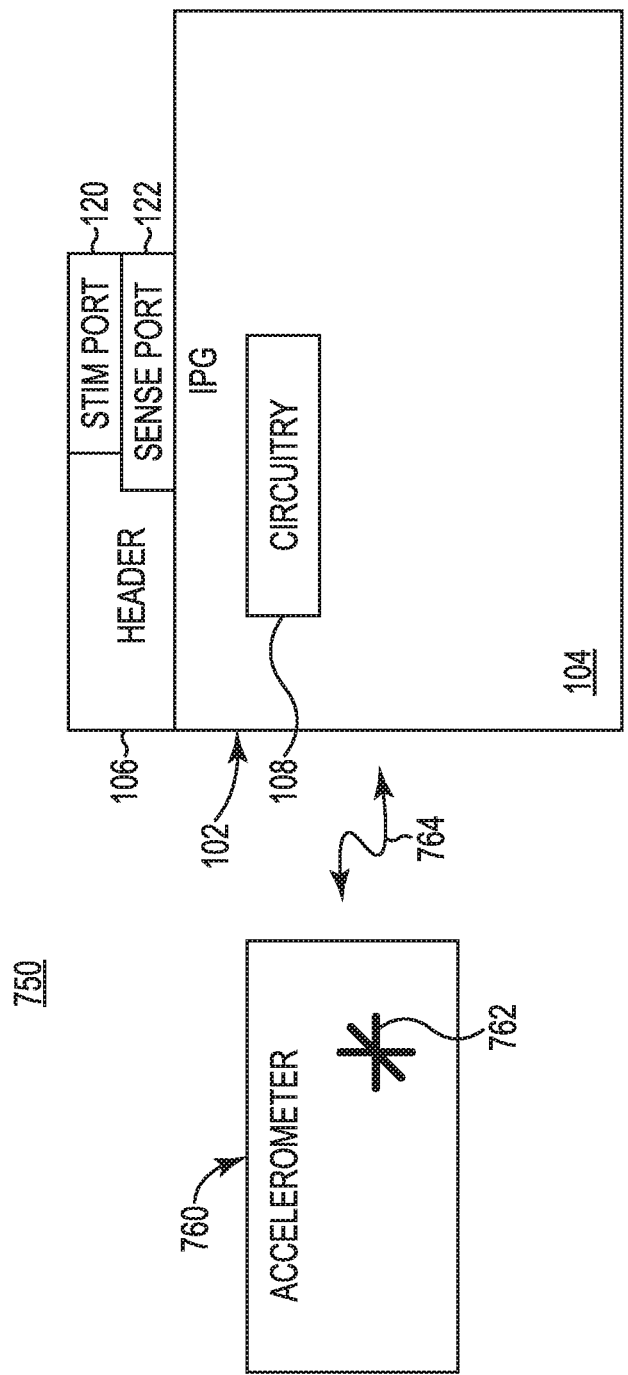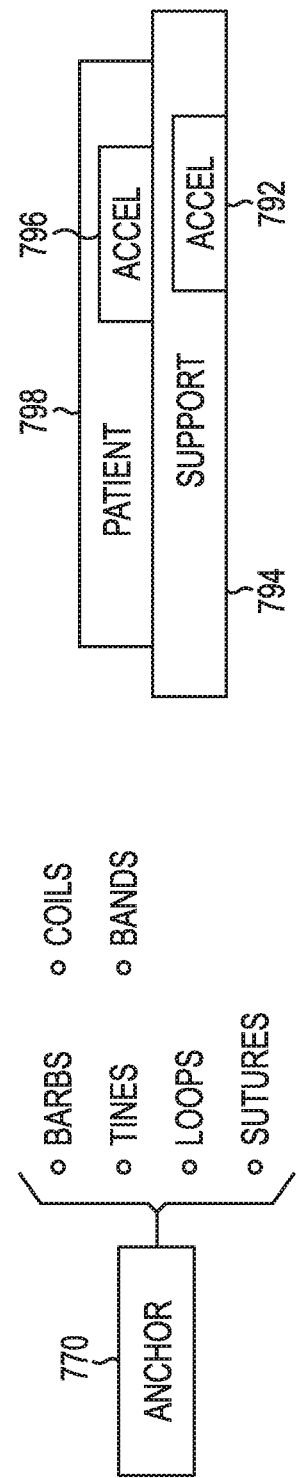

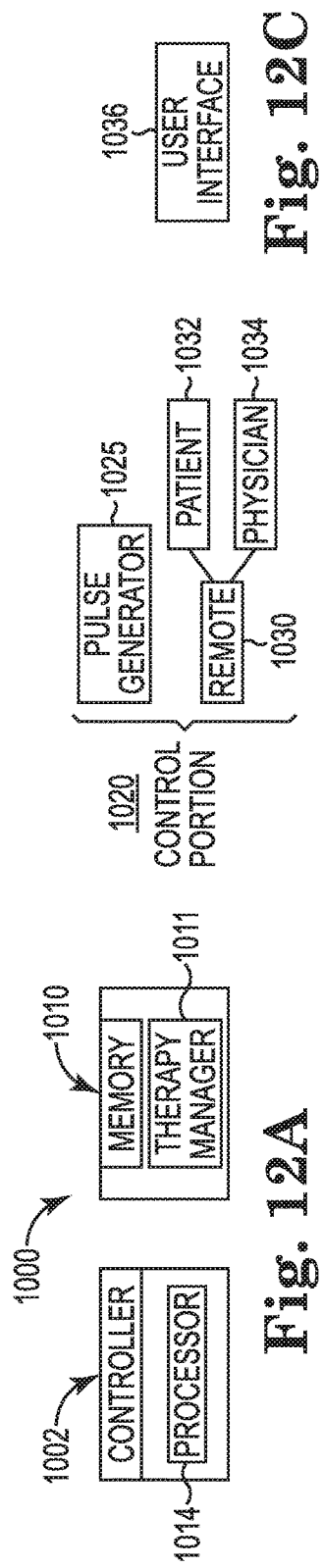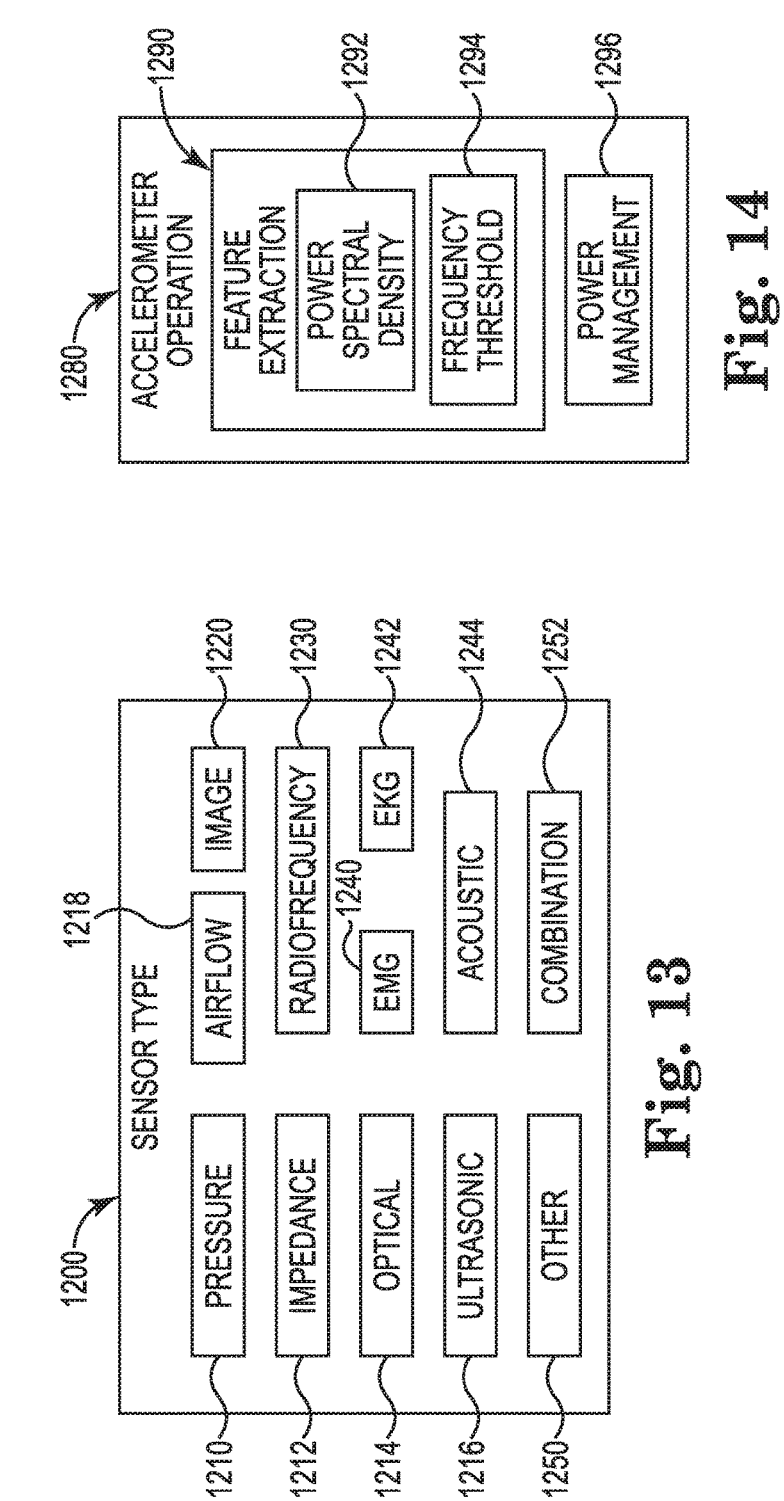

ACCELEROMETER-BASED SENSING FOR SLEEP DISORDERED BREATHING (SDB) CARE

CROSS-REFERENCE

This application is a 371 National Stage Application that claims priority to PCT Application PCT/US2017/028391, entitled "ACCELEROMETER-BASED SENSING FOR SLEEP DISORDERED BREATHING (SDB) CARE," having a filing date of Apr. 19, 2017 that claims benefit of U.S. Provisional Patent Application No. 62/324,388, entitled "ACCELEROMETER SENSOR FOR IMPLANTABLE STIMULATION THERAPY," having a filing date of Apr. 19, 2016, both of which are incorporated herein by reference.

BACKGROUND

Sensing physiologic information may enhance patient health. In some instances, such sensing may be implemented in association with treating sleep disordered breathing, which has led to improved sleep quality for some patients.

BRIEF DESCRIPTION OF THE DRAWINGS

FIG. 3 is a block diagram schematically representing an example implantable neurostimulation therapy system in a partially assembled state and including an accelerometer sensor physically coupled relative to a stimulation lead.

FIG. 4 is a block diagram schematically representing the system of FIG. 3 in an assembled state in one example.

FIG. 5 is a block diagram schematically representing an example implantable neurostimulation therapy system in a partially assembled state and including an accelerometer sensor incorporated within a header-connector of an implantable pulse generator (IPG) assembly of the system.

FIG. 6 is a block diagram schematically representing an example sensor lead including an accelerometer sensor and an anchor.

FIG. 7A is a block diagram schematically representing an example stimulation lead including a stimulation electrode and an accelerometer sensor.

FIG. 7B is a diagram including a sectional view schematically representing one example of a rotation mechanism for association with an accelerometer sensor.

FIG. 9A is a block diagram schematically representing an example system including an IPG assembly and a separate accelerometer sensor.

FIG. 9B is a diagram schematically representing an example anchor.

FIG. 9C is a diagram schematically representing one example of a patient with an implanted accelerometer sensor laying on a support.

FIG. 12A is a block diagram schematically representing an example control portion.

FIG. 12B is a diagram schematically representing at least some example different modalities of the control portion.

FIG. 12C is a block diagram schematically representing an example user interface.

FIG. 13 is a block diagram schematically representing example sensor types.

FIG. 14 is a block diagram schematically representing example accelerometer operation functions.

DETAILED DESCRIPTION

Figure 1A:
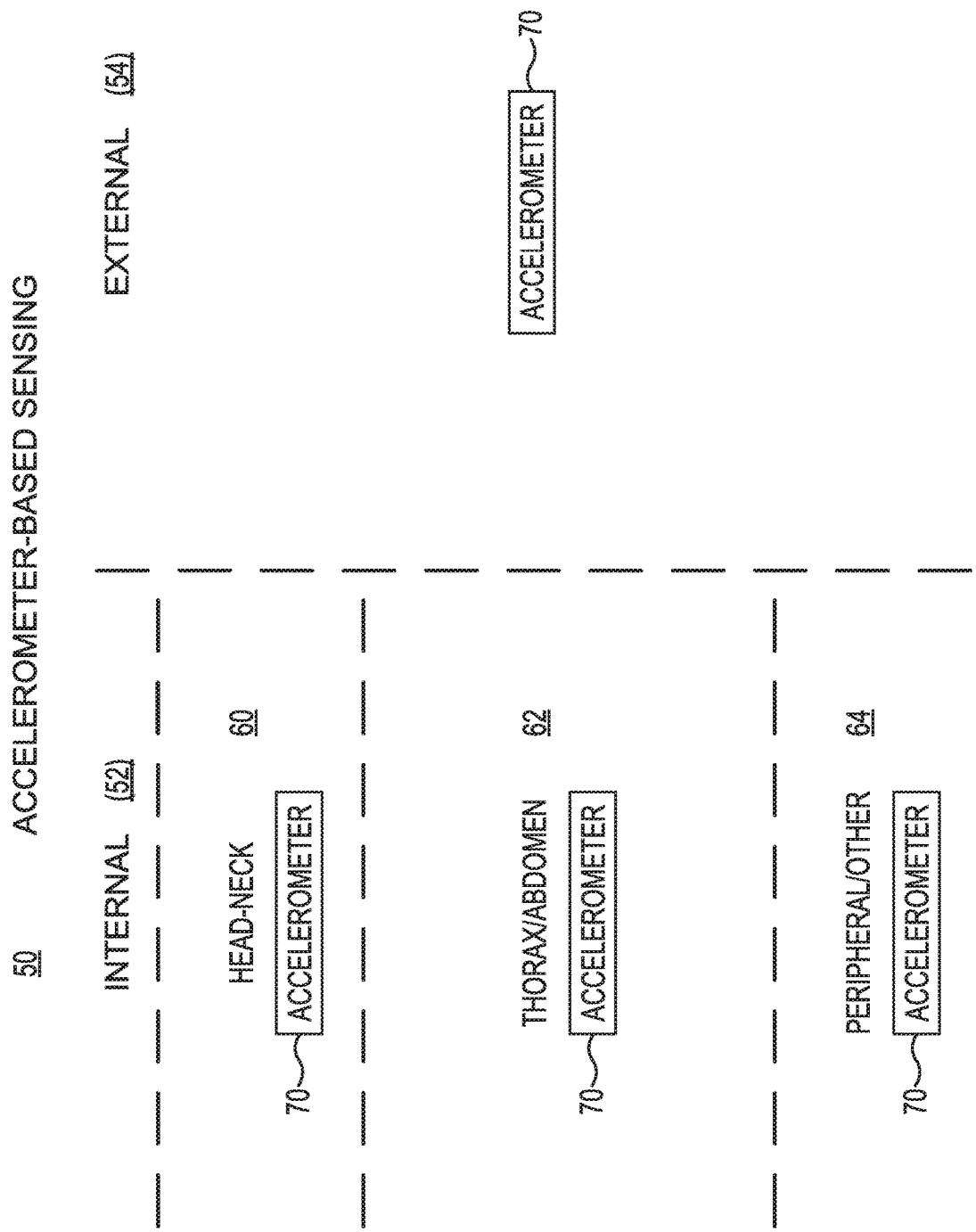
FIG. 1A is a diagram schematically representing accelerometer-based sensing, according to one example of the present disclosure.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

In at least some examples of the present disclosure, at least one sensor includes an accelerometer-based sensor, which may be employed to sense physiologic information. In some examples, this sensed physiologic information may be used for monitoring and/or evaluation of a patient. In some examples, this sensed physiologic information may be used for diagnosis, therapy, and/or therapy evaluation. In some examples, the sensed physiologic information may be employed to provide care for sleep disordered breathing, such as monitoring, evaluation, diagnosis, and/or therapy.

The accelerometer-based sensor may be external to the patient and/or may be implanted within a patient. In at least some examples, accelerometer-based sensing simplifies implantation of a sensor and/or diversifies the number and type of physiologic parameters sensed with a single type of sensor. However, in some examples, accelerometer-based sensing also can be implemented in combination with other sensor modalities, which may be external sensors and/or implantable sensors.

In at least some examples of the present disclosure, the accelerometer-based sensor forms part of a sleep disordered breathing (SDB) care device, which may be used for sensing. In some such examples, the sensing may be used for monitoring, evaluation, diagnosis, etc. without performing stimulation.

In at least some examples of the present disclosure, the accelerometer-based sensor forms part of a neurostimulation system or components thereof. In some examples, the system is used for sleep disordered breathing (SDB) therapy, such as obstructive sleep apnea (OSA) therapy. However, in some examples, the system is used for other types of neurostimulation therapy.

In some examples, a neurostimulation system, comprises an implantable pulse generator (IPG) assembly, a single lead, and a first sensing element. The single lead includes a proximal end removably connectable to a header-connector of the IPG assembly and an opposite distal end adjacent which a stimulation element is located. The first sensing element is separate from the single lead, wherein the first sensing element comprises an accelerometer-based sensor.

In some examples, the first sensing element is removably connectable to the header-connector of the IPG assembly. However, in some examples, the IPG assembly includes the above-mentioned header-connector and a housing, which contains the first sensing element. In one aspect, via these arrangements the accelerometer-based sensor can be implanted within the patient's body without tunneling used primarily to position and implant an accelerometer-based sensor. Instead, via these arrangements, such tunneling may be avoided or minimized because the accelerometer-based sensor is physically coupled relative to or contained within the IPG assembly. In addition, in some examples, these arrangements may sometimes be referred to as leadless sensing arrangements in that the accelerometer-based sensor is implanted, and physically coupled relative to the IPG assembly without a lead.

In some examples, a neurostimulation system also comprises an IPG assembly and a single lead, which includes a proximal end removably connectable to the IPG assembly. The single lead also includes an opposite distal end adjacent which (e.g. at or near) a stimulation element is located. The single lead also comprises a first sensing element, which comprises an accelerometer-based sensor. In some examples, the first sensing element is located closer to the distal end than the proximal end of the single lead. In some examples, the first sensing element is located at the distal end of the single lead. In some examples, the first sensing element is located adjacent the proximal end of the single lead. Via this arrangement, in some examples an accelerometer-based sensor may be incorporated, along with a stimulation electrode, into a single lead, thereby avoiding the use of a separate lead or separate connectable element to provide the accelerometer-based sensor.

In some examples, a neurostimulation system comprises an IPG assembly including a housing, a first lead, and a second lead. The first lead includes a proximal end removably connectable to a header-connector of the IPG assembly and an opposite distal end adjacent which (e.g. at or near) a stimulation element is located. The second lead includes a proximal end removably connectable to the IPG assembly and an opposite distal end comprising a first sensing element, which comprises an accelerometer-based sensor.

In some examples, the accelerometer-based sensor comprises the sole type of sensor of a sleep disordered breathing (SDB) care device, such as but not limited to a neurostimulation system. In some examples, the accelerometer-based sensor comprises the sole sensor (e.g. only sensor) of the care device. In some examples, the accelerometer-based sensor is the sole implantable sensor of the care device, which may or may utilize some external sensors. However, in some examples, the accelerometer-based sensor comprises just one of several types of sensor associated with or forming part of a SDB care device, such as at least some of the several types of sensors described later. Stated differently, in some examples the accelerometer-based sensor does not comprise the sole type of sensor of a SDB care device.

These examples, and additional examples, are described in more detail in association with at least FIGS. 1A-20.

FIG. 1A is a diagram 50 schematically representing accelerometer-based sensing, according to one example of the present disclosure. In some examples, the accelerometer-based sensing is associated with providing sleep disordered breathing (SDB) care.

As shown in FIG. 1A, in some examples at least one sensor includes an accelerometer-based sensor (70) located internally (52) within a patient while in some examples at least one sensor includes an accelerometer-based sensor (70) located external (54) to the patient. Such external sensors may be worn on the patient's body or spaced apart from the patient's body. In some examples, the at least one sensor including the accelerometer-based sensor may be located in a head-neck region 60, a thorax/abdomen region 62, and/or a peripheral/other region 64, as shown in FIG. 1A.

In some examples, regardless of location the respective accelerometer-based sensor(s) 70 is provided without any associated stimulation elements within or external to the patient's body. In such examples, the information sensed via the accelerometer-based sensor(s) 70 may be used for evaluating and/or diagnosing a patient.

However, in some examples, regardless of location the accelerometer-based sensor(s) 70 is provided in association with at least one stimulation element to treat sleep disordered breathing behavior and/or other physiologic conditions.

More specific example implementations of the sensor(s) shown in FIG. 1A are described and illustrated in association with at least FIGS. 1B-20.

Figure 1B:
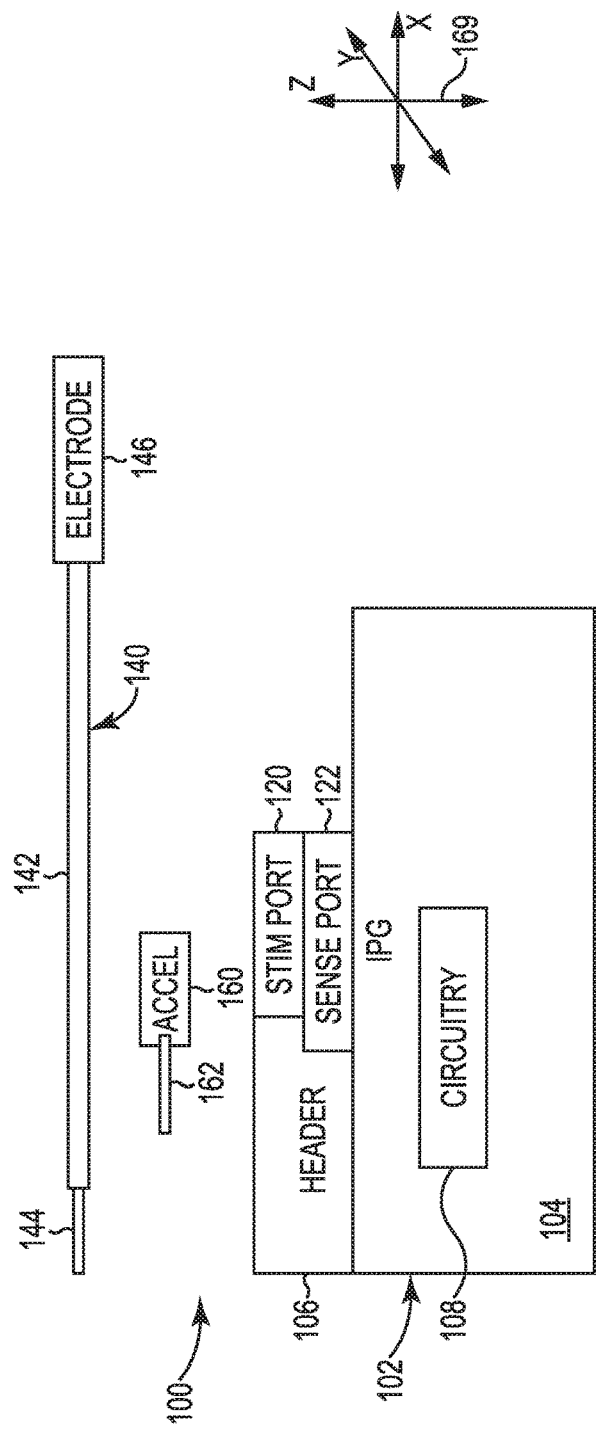
FIG. 1B is a block diagram schematically representing an example implantable neurostimulation therapy system in a partially assembled state and including an accelerometer sensor physically separate from a stimulation lead.

FIG. 1B is a block diagram schematically representing an example implantable neurostimulation therapy system 100 in a partially assembled state and including an example accelerometer-based sensor 160 physically separate from a stimulation lead 140. In some examples, the system 100 may sometimes be referred to as a care device. As shown in FIG. 1B, system 100 includes an implantable pulse generator (IPG) assembly 102, a stimulation lead 140, and an accelerometer-based sensor 160. The IPG assembly 102 comprises a housing 104 containing circuitry 108 and a header-connector 106 including a stimulation port 120 and a sensing port 122.

In some examples, accelerometer-based sensor 160 includes a proximally located plug-in connector 162, which is removably connectable relative to sensing port 122. Accordingly, physiologic information sensed via accelerometer-based sensor 160 is transmitted, via sensing port 122, to circuitry 108 of IPG. In some examples, this sensed information is used to trigger therapy, evaluate therapy, determine a need for therapeutic stimulation, etc. In some examples, this sensed information provides more general physiologic information not directly related to therapeutic stimulation. As further described later in association with at least FIGS. 11A-17, a wide variety of physiologic information can be sensed via accelerometer-based sensor 160, with such information being pertinent to the patient's well-being and/or therapy.

In some examples, the accelerometer-based sensor 160 includes a rigid, sealed housing containing an accelerometer-based sensor.

In some examples, other types of sensors are employed instead of or in combination with accelerometer-based sensor 160. These examples, and additional examples associated with the obtaining and use of sensed information are further described later in association with at least FIGS. 11A-17.

As shown in FIG. 1B, in some examples accelerometer-based sensor 160 comprises a leadless sensor. Stated differently, the accelerometer-based sensor 160 is directly coupled, both physically and electrically, relative to sensing port 122 such that, via this arrangement, no lead body is interposed between the plug-in connector 162 and the sensor 160.

In some examples, a lead body having a small length can be interposed between the plug-in connector 162 and the sensor 160. This arrangement may facilitate implantation of the IPG assembly 102. However, such a mini-length lead body would have a length not greater than a greatest dimension (e.g. length or width) of the IPG housing 104 such that the sensor 160 would still be in generally co-located with the IPG housing 104.

With further reference to FIG. 1B, the stimulation lead 140 includes a body 142 with a distally located stimulation electrode 146 and at an opposite end of body 142, a proximally located plug-in connector 144 which is removably connectable relative to stimulation port 120.

In general terms, cuff electrode 146 includes some non-conductive structures biased to (or otherwise configurable to) releasably secure the cuff electrode 1140 about a target nerve 30 (FIGS. 1-4) and includes an array of electrodes to deliver a stimulation signal to the target nerve. In some examples, the cuff electrode 1140 may comprise at least some of substantially the same features and attributes as described within at least U.S. Pat. No. 8,340,785 issued on Dec. 25, 2012 and/or U.S. Patent Publication 2011/0147046 published on Jun. 23, 2011.

In some examples, body 142 is a generally flexible elongate member having sufficient resilience to enable advancing and maneuvering the lead body 142 subcutaneously to place the electrode 146 at a desired location adjacent a nerve, such as an airway-patency-related nerve (e.g. hypoglossal nerve). In some examples, such as the case of obstructive sleep apnea, the nerves 30 may include (but are not limited to) the nerve 30 and associated muscles responsible for causing movement of the tongue and related musculature to restore airway patency. In some examples, the nerves 76 may include (but are not limited to) the hypoglossal nerve and the muscles may include (but are not limited to) the genioglossus muscle. In some examples, body 142 can have a length sufficient to extend from the IPG assembly 102 implanted in one body location (e.g. pectoral) and to the target stimulation location (e.g. head, neck). Upon generation via circuitry 108, a stimulation signal is selectively transmitted to stimulation port 120 for delivery via lead 140 to such nerves.

Accordingly, both the stimulation port 120 and the sensing port 122 of the header-connector 106 are electrically coupled relative to the circuitry 108 of IPG assembly 102 with header-connector 106 being physically coupled relative to housing 104 of IPG assembly 102.

Figure 2A:
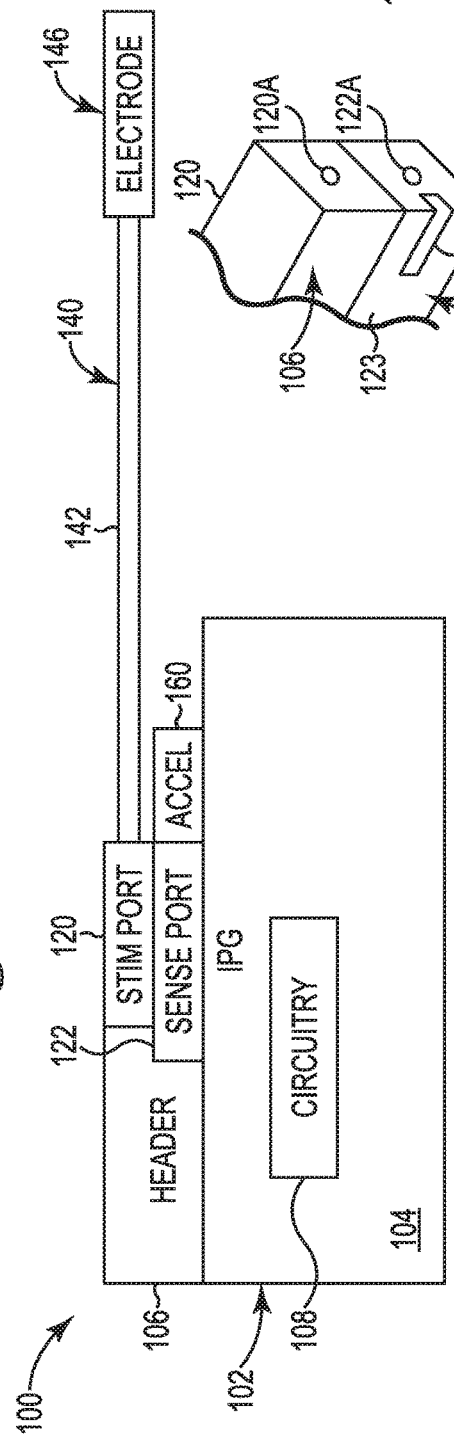
FIG. 2A is a block diagram schematically representing the system of FIG. 1B in an assembled state in one example.

FIG. 2A is a block diagram schematically representing the system 100 of FIG. 1B in an assembled state, according to one example of the present disclosure. As shown in FIG. 2A, lead 140 has been removably connected to stimulation port 120 of IPG assembly 102 while accelerometer-based sensor 160 has been removably connected to sensing port 122 of IPG assembly 102. Accordingly, accelerometer-based sensor 160 becomes physically coupled directly to the header-connector 106 of IPG assembly 102. Among other features, this arrangement may eliminate tunneling and/or other surgical steps ordinarily associated with placing sensing leads within a patient, as well as promote long term stability and ease securing the accelerometer sensor because it occurs in conjunction with securing with IPG assembly 102.

In some examples, the physical coupling of the accelerometer-based sensor 160 relative to the IPG assembly 102 is performed prior to implantation of those components.

In one aspect, in order for the accelerometer-based sensor 160 to fit on top of (e.g. next to) the housing 104 of the IPG assembly 102, a housing of the accelerometer-based sensor 160 has a size and shape that can maintain the accelerometer sensor 106 in a fixed orientation relative to the IPG assembly 102. This arrangement facilitates achieving and maintaining a proper orientation of the multiple orthogonal axes of the accelerometer-based sensor 160 relative to various axes of the patient's body, such as an anterior-posterior axis, such as more fully described later in association with at least FIG. 8B.

Figure 2B:
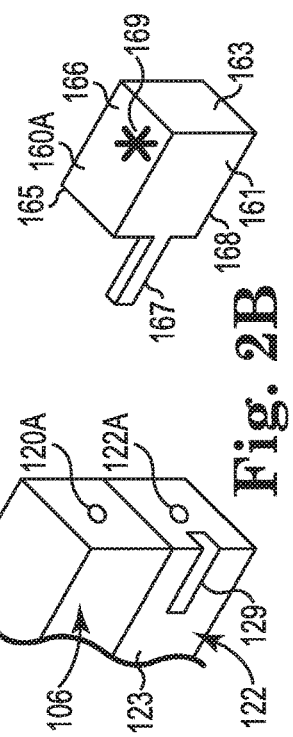
FIG. 2B is diagram including a perspective view schematically representing one example of a key mechanism associated with a header-connector of an IPG assembly and an accelerometer sensor.

FIG. 2B is diagram including a perspective view schematically representing a key mechanism associate with a header-connector of an IPG assembly and an accelerometer sensor, according to one example of the present disclosure. As shown in FIG. 2B, in some examples the stimulation port 122 comprises an assembly including a housing 123, an aperture 122A defined in housing 123 to slidably receive plug-in connector 162 of an accelerometer-based sensor 160A (like sensor 160 in FIG. 1B), and a key receiver 129 defined in housing 123. While present in FIG. 1B, plug-connector 162 is omitted in FIG. 2B for illustrative clarity.

In some examples, the accelerometer-based sensor 160A includes a housing 161 defining a top portion 166 and opposite bottom portion 168, and defining a first end portion 163 and an opposite second end portion 165, at which is defined a key 167. The key 167 is sized and shaped to be removably received within key receiver 129 of stimulation port 122 such that the accelerometer-based sensor 160A becomes mated with the stimulation port 122. In one aspect, this arrangement ensures a proper match of a particular accelerometer sensor with a particular IPG assembly. In another aspect, this key arrangement ensures that the multi-axis configuration (represented via axis indicator 169) of the accelerometer sensor is properly oriented relative to the IPG assembly 102, and therefore properly oriented relative to a patient's body. At least some examples of achieving such proper orientation are further described later in association with at least FIGS. 8A-8B.

It will be understood that, in some examples, the key arrangement may be omitted and that in some instances, the particular shape of the housing of the accelerometer-based sensor 160 may facilitate maintaining a proper orientation of the multiple axes of the accelerometer-based sensor 160 as noted above with respect to FIG. 2B.

FIG. 3 is a block diagram schematically representing an implantable neurostimulation therapy system 200 in a partially assembled state and including an accelerometer sensor 260 (like sensor 160) and stimulation lead 240, according to one example of the present disclosure. As shown in FIG. 3, system 200 comprises at least some of substantially the same features and attributes as system 100 (FIGS. 1-2), except for accelerometer sensor 260 being physically coupled relative to stimulation lead 240. In particular, as shown in FIG. 3, a proximal portion of stimulation lead 240 comprises a housing 250, which contains a proximal connection portion 252 of lead body 142 and accelerometer sensor 260. Accordingly, the accelerometer sensor 260 may sometimes be referred to as being integrated with the stimulation lead 240 or at least integrated with a connection portion of the stimulation lead 240. Stated differently, together the proximal connection portion 252 of the stimulation lead 240 and the accelerometer sensor 260 form a monolithic connection portion 250. In one aspect, the monolithic connection portion 250 forms a single unitary piece, such as via molding a housing to contain proximal connection portion 252 and accelerometer-based sensor 160.

FIG. 4 is a block diagram schematically representing the system 200 of FIG. 3 in an assembled state, according to one example of the present disclosure. As shown in FIG. 4, upon removable connection of connection portion 250 relative to header-connector 106, the proximal connection portion 252 of stimulation lead 240 becomes electrically and physically coupled relative to stimulation portion 120 and the accelerometer sensor 260 becomes electrically and physically coupled relative to sensing port 122. In some examples, the proximal connection portion 252 comprises an insert portion 144 (FIG. 3) to be removably received via the stimulation port and the accelerometer 260 comprises an insert portion 262 (FIG. 3) to be removably received via the sensing port 122.

Among other features, this arrangement reduces the number of separate elements to be handled upon implanting system 200. In one aspect, this arrangement also can ensure proper matching of a particular stimulation lead 240 with a particular accelerometer sensor 260 for a given IPG assembly 102 and/or for a particular patient. In addition, to the extent that housing 104 of IPG assembly 201 is implanted with a proper orientation (such as represented in FIG. 8B), the arrangement of accelerometer sensor 260 within connection housing 250 can ensure that the axes in the accelerometer sensor 260 has the proper orientation relative to the patient's body, such as (but not limited to) with respect to an anterior-posterior axis.

FIG. 5 is a block diagram schematically representing an implantable neurostimulation therapy system 300 in a partially assembled state and including an accelerometer sensor 360 (like sensor 160) incorporated within a header-connector 106 of an IPG assembly 102 of the system, according to one example of the present disclosure. In some examples, system 300 comprises at least some of substantially the same features and attributes as systems 100, 200 (as previously described in association with FIGS. 1-4), except for accelerometer sensor 360 being incorporated within (e.g. integrated with) header-connector 106 instead of being removably connectable relative to header-connector 106. Accordingly, via this arrangement, accelerometer sensor 360 remains on-board the IPG assembly 102 at all times, thereby preventing separation of accelerometer sensor 360 from IPG assembly 102. Like in system 200, this arrangement ensures proper matching of a particular accelerometer sensor 360 with a particular IPG assembly 102 and/or for a particular patient. However, in this arrangement, a modified stimulation lead 140 is not involved (as in FIGS. 3-4) nor is a separate accelerometer sensor involved (as in FIGS. 1-2).

With further reference to FIG. 5, in some examples the accelerometer sensor 360 comprises a multi-axis accelerometer such as a three-axis accelerometer having an orientation as indicated at 362. As noted with respect to the prior examples, the fixed, on-board location of the accelerometer sensor 360 ensures its proper orientation within the patient's body, at least to the extent that the IPG assembly 102 is implanted with a desired or proper orientation as described later in association with at least FIG. 8B.

FIG. 6 is a block diagram schematically representing a sensor lead 400 including an accelerometer sensor 460 (like sensor 160) and an anchor, according to one example of the present disclosure. As shown in FIG. 6, sensor lead 400 includes a lead body 442 extending from a proximal end 443 to an opposite distal end 445, at which is located an accelerometer sensor 460 and anchor 470. In some examples, the sensor 460 is located closer to the distal end 445 than the proximal end 443 without necessarily being at distal end 445. The proximal end 443 of sensor lead 400 is removably connectable to a sensing port 122 of an IPG assembly 102, such as in FIG. 2. Lead body 442 has at least some of substantially the same features as lead body 142 except being employed for placing accelerometer sensor 460 within a portion of a patient's body at a location some distance from the IPG assembly 102 such that the accelerometer sensor 460 is not considered to be co-located with the IPG assembly 102.

FIG. 7A is a block diagram schematically representing a stimulation lead 500 including a stimulation electrode 546 and an accelerometer sensor 560 (like sensor 160), according to one example of the present disclosure. In some examples, stimulation lead 500 comprises at least some of substantially the same features and attributes as lead 140 in FIGS. 1-2, except for additionally including an accelerometer sensor 560. As shown in FIG. 7A, lead 500 comprises a lead body 542 having a proximal end removably connectable to a port of the header-connector 106 of an IPG assembly 102 and an opposite distal end 545, at which the accelerometer sensor 560 and electrode 546 are mounted. In some examples, the sensor 560 is located closer to the distal end than the proximal end of the lead 500 without necessarily being at the distal end of lead 500.

As further shown in FIG. 7B, in some examples a portion of the lead 500 at which accelerometer sensor 560 is located includes a mechanism to enable selective rotation of the accelerometer sensor 560, which in turn, enables adopting a desired orientation of the different axes of accelerometer sensor 560. In some examples, such mechanism can be implemented as a rotatable sleeve 570 shown in FIG. 7B. In some examples, one axis of the accelerometer sensor 360 is aligned to be generally parallel to an anterior-posterior axis of the patient, which is believed to be more indicative of respiratory activity of the patient. Further information regarding such alignments is described in association with at least FIGS. 8A-8B.

It will be understood that in at least some of the examples in FIGS. 1-9D, the example accelerometer sensors are sealed for long term implantation within a patient's body, such as but not limited to hermetic sealing. In some examples, instead of or in addition to being sealed itself, a housing of an IPG assembly (FIG. 8A) containing the accelerometer sensor is sealed hermetically or via other means. In some examples in which a header-connector of an IPG assembly contains the accelerometer sensor (e.g. FIGS. 5E, 9D), at least a portion of the header-connector may be sealed hermetically or via other means.

Figure 8A:
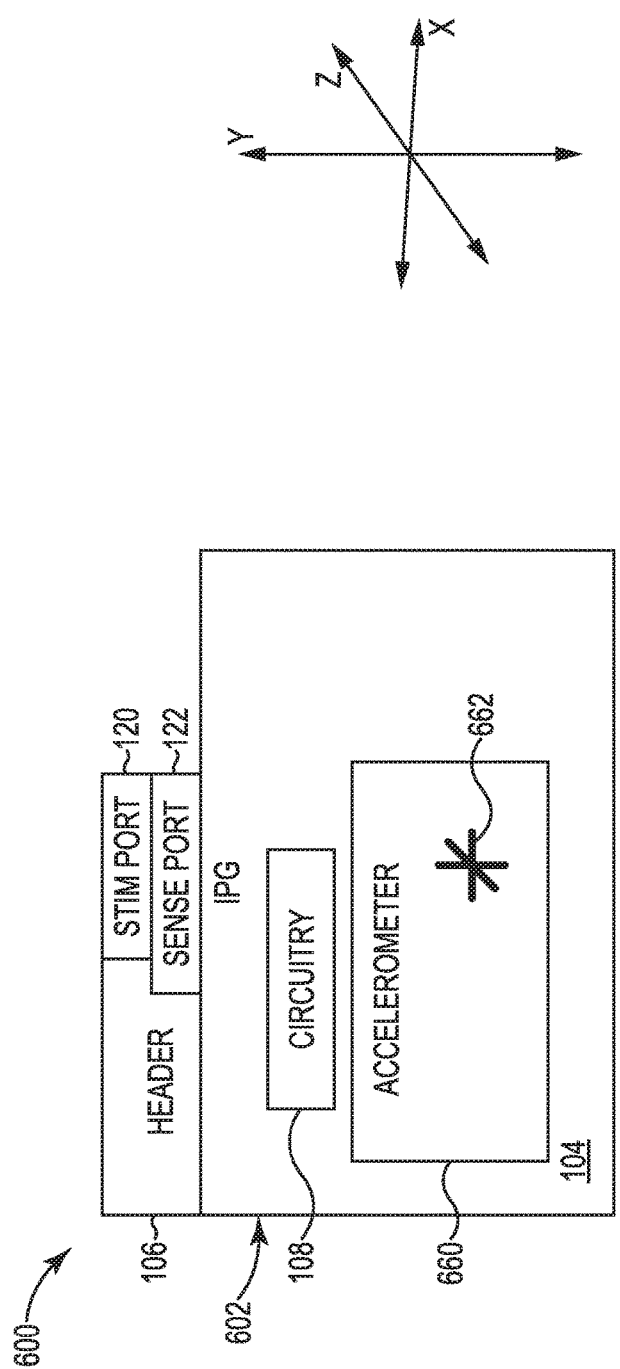
FIG. 8A is a diagram schematically representing an example IPG assembly including an accelerometer sensor incorporated within the sealed IPG housing in association with an axis orientation diagram.
Figure 8B:
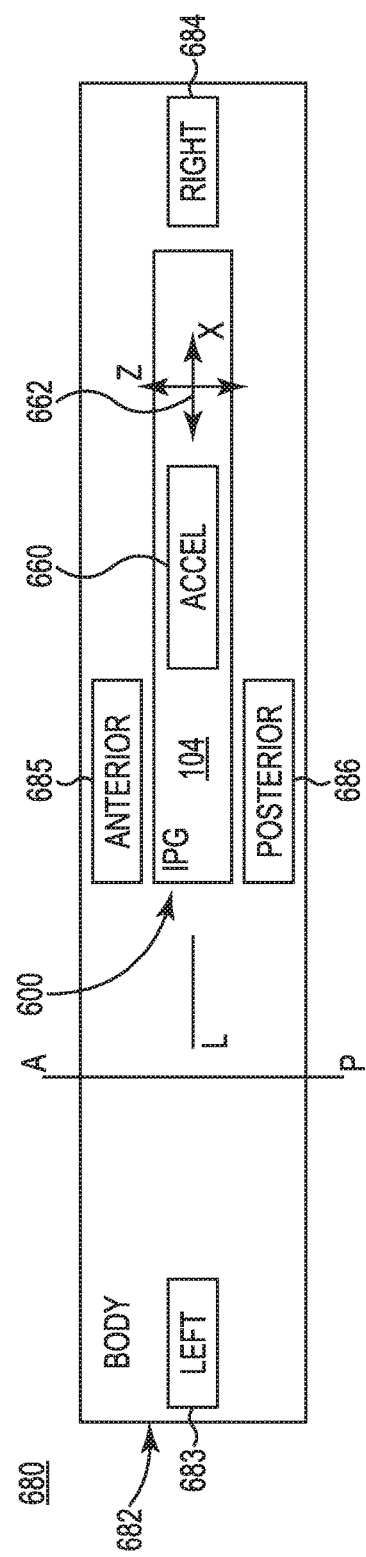
FIG. 8B is a block diagram schematically representing a sectional view of an example IPG assembly implanted within a body in association with an axis orientation diagram.

FIG. 8A is a diagram schematically representing a neurostimulation system 600 comprising an IPG assembly 602, according to one example of the present disclosure. In some examples, system comprises at least some of substantially the same features and attributes as system 300 (as previously described in association with FIG. 5), except for accelerometer sensor 660 being contained within a housing 104 of IPG assembly 602 instead of being incorporated within header-connector 106. Accordingly, via this arrangement, accelerometer sensor 660 remains on-board the IPG assembly 602 at all times, thereby preventing separation of accelerometer sensor 660 from IPG assembly 602. In addition, placing both the accelerometer sensor 660 and circuitry 108 within the housing of the IPG assembly 602 eases communication between those respective elements. Like in system 300, this arrangement also ensures proper matching of a particular accelerometer sensor 660 with a particular IPG assembly 602 and/or for a particular patient. As noted with respect to the prior examples, the fixed, on-board location of the accelerometer sensor 660 within IPG assembly 602 ensures its proper orientation within the patient's body, at least to the extent that the IPG assembly 602 is implanted with a desired or proper orientation as described later in association with at least FIG. 8B.

FIG. 8B is a block diagram 680 schematically representing a sectional view of a system 600 (including an IPG assembly 602) implanted within a body according to a desired axis orientation, according to one example of the present disclosure.

As shown in FIG. 8B, a patient's body 682 has a left side 683 and an opposite right side 684, along with an anterior portion 685 and an opposite posterior portion 686. In some examples, IPG assembly 602 is implanted such that its housing 104 causes the accelerometer sensor 660 to have a Z axis aligned generally parallel with an anterior-posterior axis (represented via line A-P) of the patient's body 682, as represented via axis orientation indicator 662. To do so, the IPG assembly 602 is implanted to cause a longitudinal axis (line L) of its housing 104 to be generally parallel to a left to right orientation of the patient's body and generally parallel to a head to toe orientation of the patient's body.

Via this arrangement, the accelerometer sensor 660 is oriented with the Z axis in line with physiologic behavior indicative of respiration, thereby enhancing sensing of respiration which, in turn enhances, therapy for sleep disordered breathing.

In some examples, one axis of an accelerometer of the accelerometer sensor 660 is generally perpendicular to a largest surface of a housing of the IPG assembly 602.

In some examples, the accelerometer-based sensor comprises a single axis accelerometer, wherein the single axis is aligned generally perpendicular to a longitudinal axis of the IPG assembly.

In some examples, the accelerometer-based sensor comprises at least two axes, wherein each respective axis is oriented at an about 45 degree angle relative to at least one of: a first surface of the housing of the IPG assembly which has a largest surface area of the IPG assembly; and a skin surface of the patient above the implanted IPG assembly after implantation. In some examples, the accelerometer-based sensor comprises at least two axes, wherein each respective axis is oriented at an about 45 degree angle relative to a plane through which a skin surface (above the accelerometer-based sensor) extends.

In some examples, the sense port 122 in header-connector 106 of IPG assembly 602 may host a second accelerometer sensor in a manner similar to one of the examples previously described in association with at least FIGS. 1-4 and 6. In some examples, the sense port 122 in header-connector 106 of IPG assembly 602 may host one of the sensor types in sensor type array 110 as described later in association with at least FIG. 13. However, in some examples, the sense port 122 in IPG assembly 602 is omitted entirely from the design and construction header-connector 106 or is otherwise permanently sealed.

FIG. 9A is a block diagram schematically representing a system including an IPG assembly 102 and a separate accelerometer sensor 760, according to one example of the present disclosure. In some examples, the IPG assembly 102 comprises at least some of substantially the same features and attributes as IPG assembly 102 as previously in association with FIG. 1B. Accelerometer sensor 760 comprises at least some of substantially the same features and attributes as the previously described accelerometer sensors, except for the lack of physical coupling of accelerometer sensor 760 relative to IPG assembly 102 and except for accelerometer sensor 760 being electrically and communicatively coupled wirelessly relative to IPG assembly 102.

In a manner similar to the example of FIG. 8A, in system 750 sense port 122 may be omitted or used for a second sensor, which can be one of the sensor types of array 1100 in FIG. 13 or a second accelerometer sensor in the manner of the example accelerometer sensors in FIGS. 1-6.

In some examples, circuitry 108 of IPG assembly 102 and accelerometer sensor 760 communicate via a wireless communication pathway 780 according to known wireless protocols, such as Bluetooth, NFC, 802.11, etc. with each of circuitry 108 and accelerometer sensor 760 including corresponding components for implementing the wireless communication pathway 780. In some examples, a similar wireless pathway is implemented to communicate with devices external to the patient's body for at least partially controlling the accelerometer sensor 760 and/or the IPG assembly 102, to communicate with other devices (e.g. other sensors) internally within the patient's body, or to communicate with other sensors external to the patient's body.

Figure 9D:
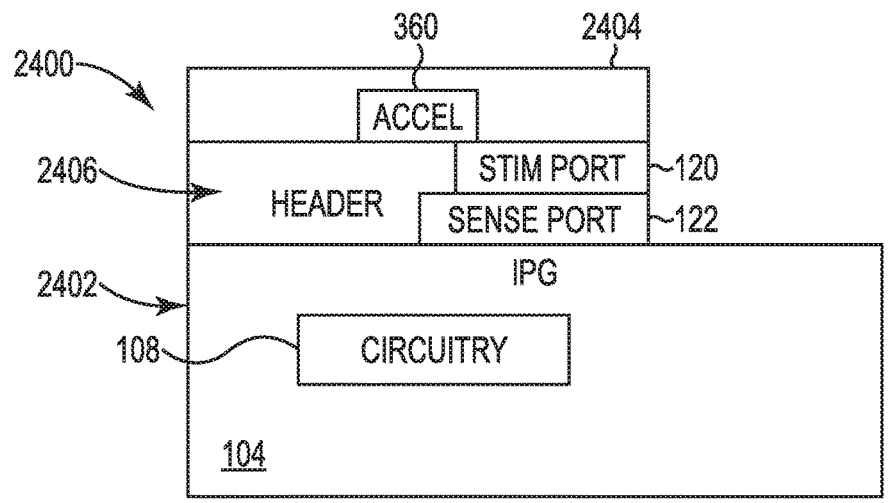
FIG. 9D is a block diagram schematically representing an example IPG assembly having an accelerometer sensor incorporated with a header-connector.

While just one accelerometer sensor 760 is shown in FIG. 9A, it will be understood that in some examples, at least two such accelerometer sensors 760 can be implanted in the patient's body to enable operation in a differential mode (e.g. 870 or 950 in FIG. 11E) or to provide more complex physiologic signal vectors from which diagnostic and/or therapeutic information can be obtained. In some examples, the second accelerometer also can be one of the sensors described in the examples of FIGS. 1-8B or 9D.

As shown in FIG. 9A, the accelerometer sensor 760 includes an axis orientation indicator 762 by which the accelerometer sensor 760 can be implanted according to a desired axis orientation, such as but not limited to, according to the principles of axis orientation similar to that described in association with FIGS. 8A-8B.

As shown in FIG. 9B, in some examples an anchor 790 is provided as part of system 750 to facilitate anchoring accelerometer sensor 760 at a desired location, and at a desired axis orientation, within the patient's body. As shown in FIG. 9B, the anchor 790 can include barbs, tines, loops, sutures, coils, and/or bands, etc. which can be selectively deployed upon or after establishing the desired location and orientation of the accelerometer sensor 760. In some examples, the anchor 790 is removably couplable to the accelerometer sensor 760 while in some examples, the anchor 790 is integrated with (i.e. not physically separable from) a housing of the accelerometer sensor 760. In some examples, anchor 790 is secured relative to a bony structure in the patient's body while in some examples, anchor 790 is secured relative to non-bony structures in the patient's body.

Regardless of the type of accelerometer sensor in the various examples of the present disclosure as schematically represented via at least FIGS. 1-9D, in some examples at least one of the various accelerometer sensors is implanted within the patient's body while another accelerometer sensor (e.g. 760 in FIG. 9A) is external to the body, such as being worn on the body via a garment, belt, wristband, wristwatch, wearable smartphone, wearable smartwatch, etc. By looking at the difference in information obtained from both such accelerometers sensors, one can better determine characteristics of a sensed accelerometer which are best representative of a respiratory information or other information related to diagnosing and treating sleep disordered breathing.

In some examples, as shown in FIG. 9C, one external accelerometer sensor 792 has a fixed location within a support 794, such as a portion of a bed, on which the patient sleeps and another accelerometer sensor 796 is implanted within the patient's body. Differences and similarities in the respective signals, at different points in time depending on the patient's posture, may be indicative of diagnostic and/or therapeutic information related to sleep disordered breathing.

FIG. 9D is a block diagram schematically representing a neurostimulation system 2400 including an IPG assembly 2402 having an accelerometer sensor 360 incorporated with a header-connector 2406, according to one example of the present disclosure. In some examples, system 2400 comprises at least some of substantially the same features and attributes as system 300 in FIG. 5, except with the accelerometer sensor 360 being coupled to header-connector 2406 without replacing the sense port 122. Instead, a housing portion 2404 is coupled to or integrated with header-connector 2406, with housing portion 2404 containing accelerometer sensor 360. Via this arrangement, the accelerometer sensor 360 can be added to IPG assembly 2402 without altering housing 104 or circuitry 108 and while still retaining sense port 122 to connect other sensors to IPG assembly 2402, such as a second accelerometer sensor or one of the sensors in the array 1100 in FIG. 13.

Figure 10:
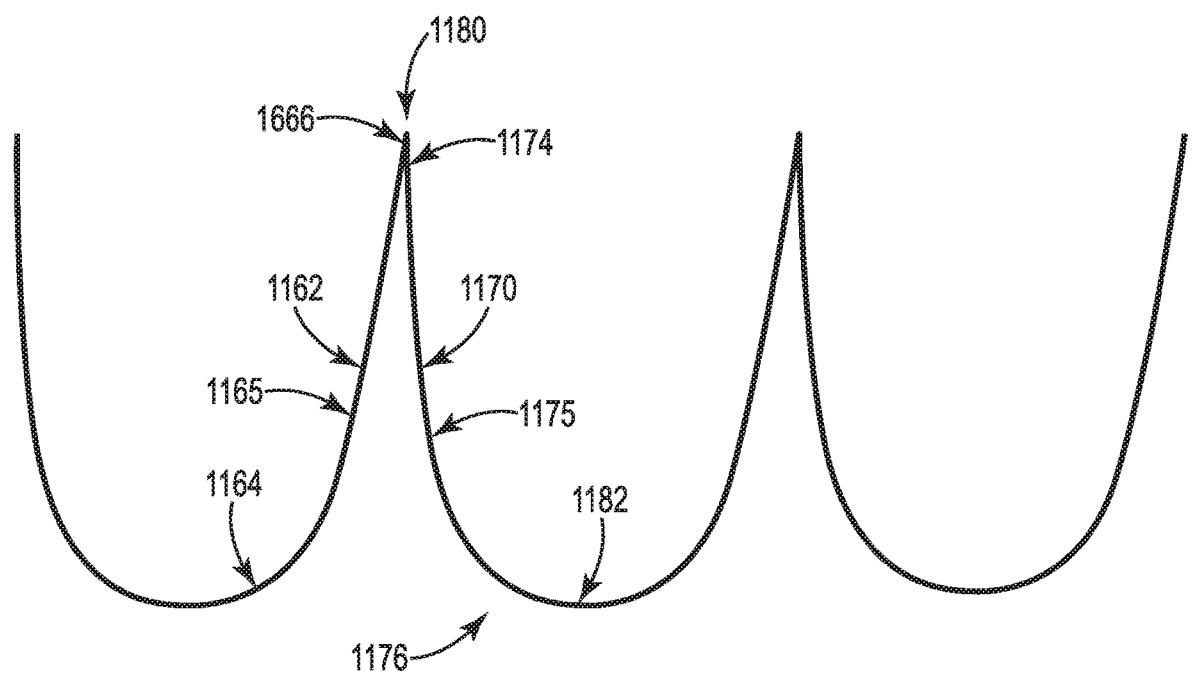
FIG. 10 is a diagram schematically representing an example respiratory waveform.

FIG. 10 is a diagram 700 schematically representing a respiratory waveform 1150, according to one example of the present disclosure. Of course, variances may exist from patient-to-patient so it will be understood that the breathing pattern illustrated in respiratory waveform 1150 is a representative example provided for illustrative purposes and is not intended to strictly define a breathing pattern that is universally normal for all patients. Rather, respiratory waveform 1150 is primarily provided as a reference for understanding some aspects of further examples of the present disclosure as described in association with at least FIGS. 11A-19 and/or the examples previously described in association with at least FIGS. 1-9E.

In the example of breathing pattern 1150 shown in FIG. 10, a respiratory cycle 1160 includes an inspiratory phase 1162 and an expiratory phase 1170. The inspiratory phase 1162 includes an initial portion 1164, intermediate portion 1165, and end portion 1666 while expiratory phase 1170 includes an initial portion 1174, intermediate portion 1175, and an end portion 1176. In some instances, the initial portion 1164 is sometimes referred to as inspiration onset or onset of inspiration while the initial portion 1174 is sometimes referred to as expiration onset or onset of expiration.

A first transition 1180 occurs at a junction between the end inspiratory portion 1166 and the initial expiratory portion 1174 while a second transition 1182 occurs at a junction between the end expiratory portion 1176 and the initial inspiratory portion 1164. In some instances, end expiratory portion 1176 includes and/or is referred to as an expiratory pause that occurs just prior to inspiration onset, i.e. initial inspiratory portion 1164.

It will be understood that, in some examples, the various example implementations of accelerometer sensors (and their associated IPG assembly/systems) as previously described in association with at least FIGS. 1-9E may be used to monitor respiration, detect and treat sleep disordered breathing (SDB), as well as other physiologic information related to the patient's general well-being and/or related to the treatment or evaluation of sleep disordered breathing. Accordingly, the following examples as described in association with at least FIGS. 11A-17 are provided to further describe at least some example implementations in which information sensed via the previously described accelerometer sensors may be used.

Moreover, each of the various engines, functions, parameters, etc. as described in association with at least FIGS. 11A-17 can be implemented via, or at least partially controlled via, a control portion and/or user interface as further described later in association with at least FIGS. 12A-12C.

Figure 11A:
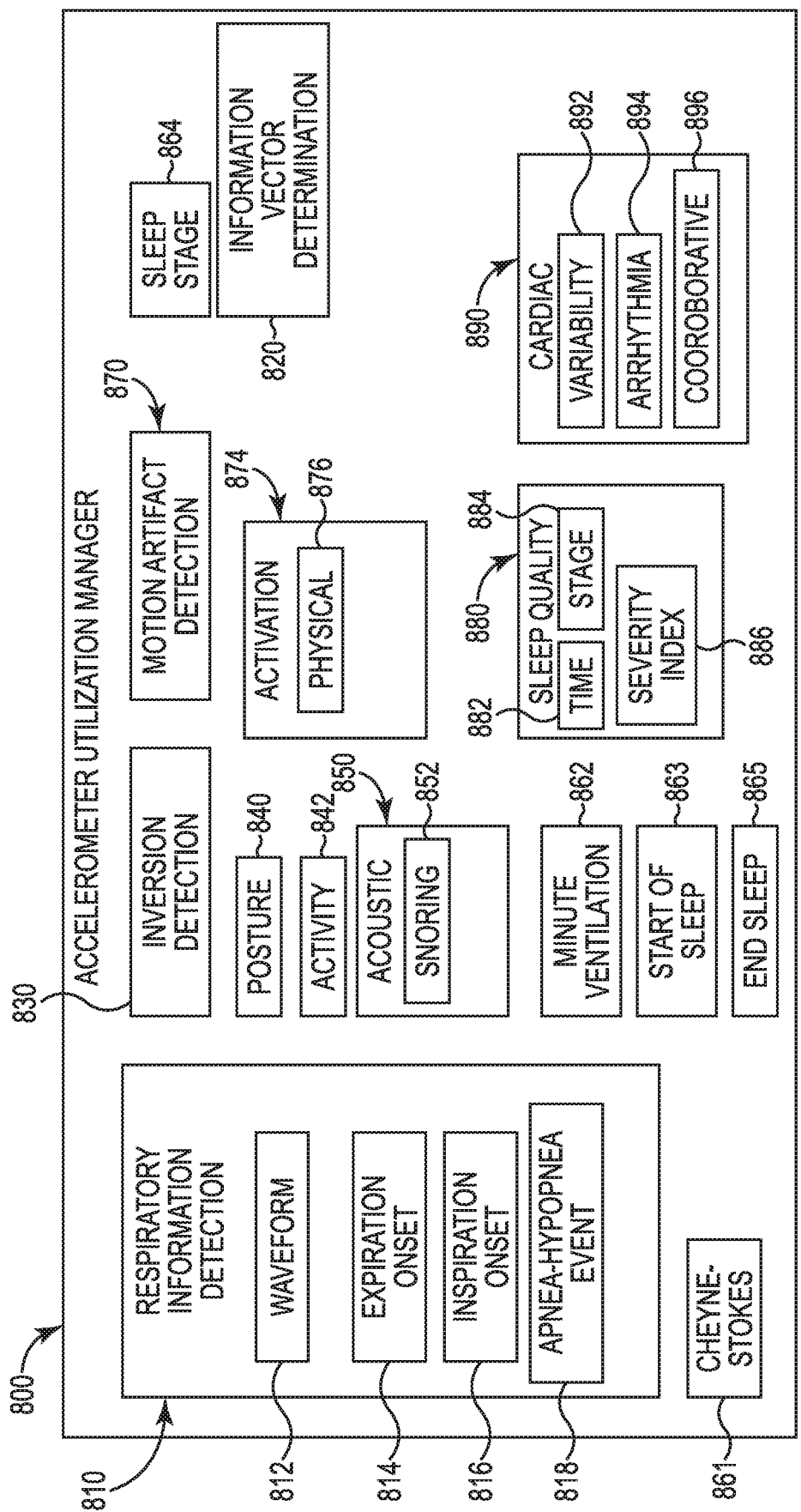
FIG. 11A is a diagram schematically representing an example accelerometer utilization engine.

With this in mind, reference is made to FIGS. 11A-17. FIG. 11A is a diagram schematically representing an accelerometer utilization manager 800, according to one example of the present disclosure. As shown in FIG. 11A, in some examples the accelerometer utilization manager 800 comprises a respiratory information detection engine 810, which includes a waveform function 812, an expiration onset parameter 814, an inspiration onset function 816, and an apnea-hypopnea event detection engine 818. In some examples, the apnea-hypopnea event detection engine 818 is implemented via an apnea-hypopnea event detection engine 1300 as described later in association with at least FIG. 15. In some examples, the respiration information detection engine 810 may comprise a respiration monitor and/or may sometimes be referred to as a respiration monitor.

In some examples, in general terms via waveform function 812 the respiratory information detection engine 810 detects and tracks a respiratory waveform, including but not limited to, detecting and tracking a respiratory rate, such as the time between onsets of inspiration or as the time between onsets of expiration. Accordingly, via waveform function 812, the respiratory information detection engine 810 can obtain a wide range of information, features, and characteristics discernible from a respiratory waveform sensed via one of the example accelerometer sensor arrangements and/or other types of sensors (FIG. 13).

Within this wide range of information, at least two characteristics of a respiratory waveform can play a prominent role in diagnosis, evaluation, and treatment of sleep disordered breathing. Accordingly, the respiratory information detection engine 810 includes an expiration onset function 814 and an inspiration onset function 816.

Accordingly, in some examples the expiration onset function 814 of respiration information detection engine 810 in FIG. 11A can detect onset of expiration according to at least one of: (A) a second derivative of an amplitude of a respiration signal below a threshold (e.g. the sharpest peak); (B) a time after an onset of inspiration; and (C) a moving baseline for which time is calculated using the time of previous cycles and a respiratory rate. For instance, in some examples a respiration signal corresponds to a single axis (e.g. Z axis) of the accelerometer sensor, from whose output an amplitude can be determined and from which further processing may be applied, such as determining first and second derivatives.

Via this arrangement, the onset of expiration can be determined, and then used to trigger or terminate stimulation therapy as well as be used as a fiducial for general timing of respiratory evaluation and/or other therapeutic functions.

In some examples, prior to applying the above scheme, the signal may be processed with a lowpass and/or highpass filter to reject higher frequency motion artifact and lower frequency signals due to orientation with respect to the earth's gravity.

In some examples, the inspiration onset function 816 of respiration information detection engine 810 in FIG. 11A can detect onset of inspiration according to at least one of: (A) identification, after expiration onset, of a derivative of amplitude of respiration above a threshold; (B) time after onset of expiration: and (C) a moving baseline for which time is calculated using the time of previous cycles and a respiratory rate. Via this arrangement, the onset of inspiration can be determined, and then used to trigger or terminate stimulation therapy as well as be used as a fiducial for general timing of respiratory evaluation and/or other therapeutic functions. In some examples, prior to applying the above scheme, the signal may be processed with a lowpass and/or highpass filter to reject higher frequency motion artifact and lower frequency signals due to orientation with respect to the earth's gravity.

It will be understood that in some examples, both inspiration onset and expiration onset are used in combination as part of a more general scheme to trigger or terminate stimulation therapy as well as be used as a fiducial for general timing of respiratory evaluation and/or other therapeutic functions.

In some examples, a respiration monitor associated with at least one sensor is used to determine, at least one of an inspiratory phase and an expiratory phase, based on respiration information including at least one of respiratory period information and respiratory phase information. In some examples, a pulse generator is used to selectively stimulate an upper airway patency-related nerve via a stimulation element, during a portion of the inspiratory phase, based on respiration information from the respiration monitor. In some such examples, the pulse generator is optionally implantable.

Figure 16:
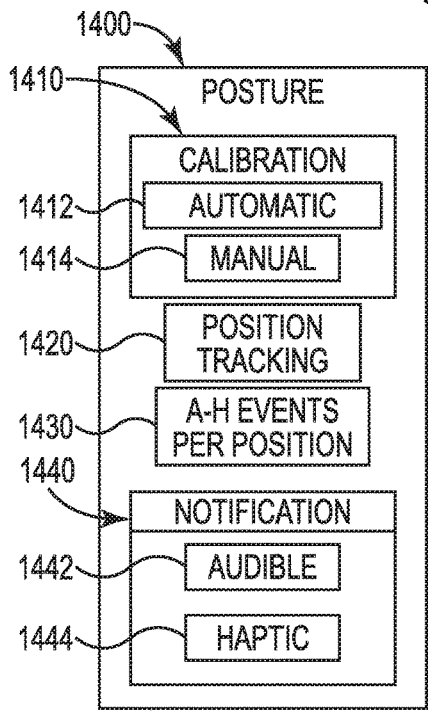
FIG. 16 is a block diagram schematically representing an example posture information engine.

In some examples, as shown in FIG. 11A the accelerometer utilization manager 800 comprises an inversion detection engine 830. In some instances, a sensed respiratory signal may be inverted due to posture changes, which may occur depending on the axis orientation of the accelerometer sensor relative to a surface the patient is resting on. In some examples, such posture information is obtained in association with the later described posture function 840 (FIG. 11A), posture sensing function 900 (FIG. 11B), and/or posture engine 1400 (FIG. 16).

Such inverted signals exhibit inspiration as having a predominantly negative slope and exhibit expiration as having a predominantly positive slope. In some examples, additional criteria (for declaring an inverted signal) include a duration of the positive slope portion of the waveform being longer than a duration of the negative slope portion of the waveform, as might be observable over several respiratory cycles. In some examples, additional criteria (for declaring an inverted signal) include a value of the mean of the signal being greater than a midpoint value, in which the midpoint is defined as one-half of a peak-to-peak amplitude. In the some examples, additional criteria (for declaring an inverted signal) include a maximum of absolute value of a second derivative at a location where the respiration signal is less than a respiration midpoint value.

By detecting an inverted respiratory waveform, the system may ensure that accurate tracking of patient respiration occurs, which in turn, may ensure that tracking and/or determinations made by the various engines, functions, parameters (FIG. 11A-17) based on sensed respiratory information are sound.

In some examples, accelerometer utilization manager 800 comprises a posture function 840. In at least this context, the term posture refers at least to identifying whether a patient is in a generally vertical position or a lying down position, such as a supine position, a prone position, a left side position (e.g. left lateral decubitus), a right side position (e.g. right lateral decubitus), as further described in association with at least FIG. 11B. In some instances, the term posture may sometimes be referred to as "body position." Among other uses, some of which are detailed in association with FIG. 16 and elsewhere within the present disclosure, sensed posture information may be indicative of behaviors from which sleep quality information or sleep disordered breathing (SDB) information may be determined.

In some examples, the posture function 840 rejects non-posture components from an accelerometer sensor signal via low pass filtering relative to each axis of the multiple axes of the accelerometer sensor. In some examples, posture is at least partially determined via detecting a gravity vector from the filtered axes.

In some examples, accelerometer utilization manager 800 comprises an activity function 842, which can determine whether the patient is engaged in physical activity such as walking, running, swimming, etc. and determine related information such as total caloric expenditure. In some examples, such tracked information may provide a measure of overall health, overall health correlated with sleep disordered breathing therapy effectiveness, and/or other diagnostic information. In some examples, a sampling rate is increased when activity levels are changing quickly (e.g. measured values of sequential samples changes) and is decreased when the measured value of sequential samples are relatively stable. In some examples, the activity function 842 operates in cooperation with other functions, such as posture function 840 (FIG. 11A) and posture information detection engine 1400 (FIG. 16).

In some examples, one potential classification protocol includes determining whether the patient is active or at rest via the posture function 840 (e.g. 902 in FIG. 11B) and/or activity function 842 in FIG. 11A. In some examples, when a vector magnitude of the acceleration measured via the accelerometer-based sensor meets or exceeds a threshold (optionally for a period of time), the measurement may indicate the presence of non-gravitational components indicative of non-sleep activity. In some examples, the threshold is about 1.15 G. Conversely, measurements of acceleration of about 1 G (corresponding to the presence of the gravitational component only) may be indicative of rest. In some examples, the posture function 840 may reduce sampling to about 4 Hz to reduce processing power consumption.

In some examples, one potential classification protocol implemented via the posture function (e.g. 840 in FIG. 11A, 900 in FIG. 11B) includes determining whether at least an upper body portion (e.g. torso, head/neck) of the patient is in a generally vertical position (e.g. upright position) or lying down per parameter 904. In some examples, a generally vertical position may comprise standing or sitting. In some examples, this determination may observe the angle of the accelerometer-based sensor between the y-axis and the gravitational vector, which sometimes may referred to as a y-directional cosine. In the example, when such an angle is less than 40°, the measurement suggests the patient is in a generally vertical position, and therefore likely not asleep.

In some examples, processing this posture information may include excluding an inverted position, such as via inversion detection engine 830 in FIG. 11A.

In some examples, if the measured angle (e.g. a y-directional cosine) is greater than 40 degrees, then the measured angle indicates that the patient is lying down per parameter 904. In this case, one example protocol associated with the posture functions (e.g. 840 in FIG. 11A, 900 in FIG. 11B) includes classifying sub-postures, such as whether the patient is in a supine position (e.g. 906 in FIG. 11B), a prone position (e.g. 908 in FIG. 11B), or in a lateral decubitus position (e.g. 910, 912 in FIG. 11B). In some examples, the protocol seeks to determine as soon as possible if the patient is in a supine position, which may be more likely to produce sleep disordered breathing.

Accordingly, after confirming a likely position of lying down, the protocol determines if the patient is in a supine position (906) or a prone position (908). In some examples, the determination of a supine state is made when an absolute value of the z-directional cosine (the angle of the an accelerometer-based sensor between the z-axis (calibrated to represent the anterior-posterior axis of the patient's body) and the gravitational vector is less than or equal to 45 degrees and the determination of a prone state is made when the absolute value of the z-directional cosine is greater than or equal to 135 degrees.

If neither of those criteria are satisfied, then the patient may be lying on their left or right side (e.g. lateral decubitus positions 910, 912). Accordingly, the protocol performs a further classification via the pitch angle such that the patient is lying on their right side if the pitch angle is less than or equal to negative 45 degrees or greater than or equal to negative 135 degrees. However, the protocol determines that the patient is lying on their left side if the pitch angle is greater than or equal to 45 degrees or the pitch angle is less than or equal to 135 degrees. In some examples, a similar determination may be made using directional cosines.

In some examples, accelerometer utilization manager 800 comprises an acoustic engine 850 to determine if snoring is occurring per snoring function 852. One arrangement in which acoustic engine 850 may determine snoring corresponds to placement of the accelerometer sensor at the distal end of a stimulation lead (e.g. stimulation lead 500 in FIG. 7A), which is secured to an upper airway-patency related nerve. Via this arrangement, the accelerometer sensor will be located in close physical proximity to the physical manifestations and effects of snoring at the upper airway. In some examples, a similar snoring-pertinent placement of the accelerometer sensor can be made when the accelerometer sensor is physically independent of a lead or the IPG assembly 102, such as in the system 750 of FIG. 9A.

In some examples, acoustic engine 850 can use other acoustically-sensed information such as an acoustic sensor 1244 as described later in association with at least FIG. 13. This other acoustic information may be used in addition to, or instead of, the acoustic information obtained via one of the example accelerometer sensor implementations.

In some examples, the accelerometer utilization manager 800 comprises a minute ventilation engine 862 to determine and/or track minute ventilation, which can provide a correlation of motion with tidal volume and act as a significant corollary to apnea detection.

In some examples, the accelerometer utilization manager 800 comprises a Cheyne-Stokes respiration engine 861 to determine and/or track Cheyne-Stokes respiration, which can provide a correlation of motion with changes in tidal volume and act as a significant corollary to apnea detection.

In some examples, accelerometer utilization manager 800 comprises a start-of-sleep detection engine 863. In some instances, start-of-sleep may sometimes be referred to as sleep onset. Via engine 863, once a treatment period has been initiated, delivery of stimulation is delayed until start-of-sleep has been detected. Doing so can facilitate the patient falling asleep before the first therapeutic stimulation occurs while also preventing therapeutic stimulation from beginning too late. In some examples, detecting start-of-sleep via engine 863 is implemented via tracking posture (e.g. 840 in FIG. 11A; 1400 in FIG. 16), activity (e.g. 842 in FIG. 11A), cardiac information (e.g. 890, 892 in FIG. 11A), and/or trends of respiratory rates (e.g. 810 in FIG. 11A). In some examples, engine 863 is subject to a manual therapy activation function controllable by a patient such that therapy may not be initiated even when start-of-sleep is detected if the patient has implemented an off or "no therapy" mode. In some examples, this manual therapy activation function can ensure that stimulation therapy does not become initiated during non-sleep hours when the patient is relatively sedentary (e.g. prolonged sitting, driving, etc.) or in a horizontal position, such as laying in a dentist chair, laying on the beach, and the like.

In some examples, accelerometer utilization manager 800 comprises a motion artifact detection engine 870. In one aspect, motion signals have a significantly greater amplitude than respiration signals, and therefore the motion signals are extracted from a respiratory waveform or otherwise rejected. In some examples, this extraction may be implemented via an awareness of motion associated with an X axis or Y axis of an accelerometer sensor having signal power significantly greater than the signal power of a Z axis in the accelerometer sensor, such as where the accelerometer sensor is implanted in some examples such that its Z axis is generally parallel to an anterior-posterior axis of the patient's body. If a patient's respiration signal is largest in a particular axis (not necessarily aligned with one of X, Y, Z), motion artifact can be rejected by filtering signals not aligned with the axis where respiration is largest. In one aspect, motion signals sensed via the accelerometer sensor can be distinguished from the respiration signals sensed via the accelerometer sensor according to the high frequency content above a configurable threshold.

In some examples, accelerometer utilization manager 800 comprises an activation engine 874. In some examples, the activation engine 874 provides at least partial control over therapy, such as when a remote control (physician or patient) is not available. Such partial control includes at least pausing therapy, starting therapy, stopping therapy, and the like. In some examples, the activation engine 874 operates according to physical control mode 876, such as tapping the chest (or pertinent body portion at which the accelerometer sensor is located) a certain number of times within a configurable time period (e.g. three strong taps within two seconds). In some examples, this physical control mode 876 may act as an alternate therapy deactivation mechanism, such as when the stimulation system (including IPG assembly 102) is accidentally activated, such as upon an incorrect determination of sleep via an automatic therapy initiation mechanism.

In some examples, accelerometer utilization manager 800 comprises a sleep stage determination engine 864 by which sleep stages can be determined. In some examples, such determination is made according to the relative stability of respiratory rate throughout the treatment period (during sleeping hours). In some examples, engine 864 determines and tracks the number of minutes awake, minutes in bed, posture, sleep/wake cycle, and/or number and depth of REM periods. In some examples, accelerometer utilization manager 800 comprises a sleep quality engine 880 to determine sleep quality according to a combination of a sleep time parameter 882, a sleep stage parameter 884, and a severity index parameter 886 (e.g. AHI measurement). In some instances, the determined sleep quality is communicated to at least the patient to affirm the patient when sleep quality is good and to encourage and challenge the patient when sleep quality is poor. The communication may suggest lifestyle changes and/or increased therapy compliance.

In some examples, a sleep function (e.g. 864 in FIG. 11A) may determine, at least partially via at least one sensing element, sleep stages in which a determination of at least some of the determined sleep stages may be implemented via at least one of activity information, posture information, respiratory rate information, respiratory rate variability (RRV) information, heart rate variability (HRV) information, and heart rate information.

In some examples, accelerometer utilization manager 800 comprises a cardiac detection engine 890 including a variability parameter 892, an arrhythmia parameter 894, and a corroborative parameter 896. In some examples, accelerometer 160 enables acoustic detection of cardiac information, such as heart rate. In some examples, measuring the heart rate includes sensing heart rate variability (934 in FIG. 11C) per parameter 892 (FIG. 11A).

In some examples, accelerometer 160 enables detection of cardiac information via a seismocardiogram (922 in FIG. 11C) or a ballistocardiogram (e.g. 924 in FIG. 11C) waveforms, including QRS complexes. In some examples, this cardiac information may provide heart rate variability information per heart rate variability sensing function 930 (FIG. 11C) and parameter 892 (FIG. 11A).

In some examples, via one of the accelerometer sensors, one can sense respiratory information, such as but not limited to, a respiratory rate. In some examples, whether sensed via an accelerometer sensor alone or in conjunction with other sensors, one can track cardiac information and respiratory information simultaneously by exploiting the behavior of manner in which the cardiac waveform may vary with respiration.

In some examples, the variability parameter 892 tracks heart-rate variability. In some examples, the heart-rate variability may correlate with autonomic function. In one aspect, tracking such heart-rate variability (HRV) is based on a strong beat-detection method providing reasonably accurate R—R intervals and associated cardiac trends. It will be understood that R represents a peak of a QRS complex of a cardiac waveform (e.g. an ECG wave, seismocardiogram, or ballistocardiogram), and the R—R interval corresponds to an interval between successive "R"s in the cardiac waveform.

Figure 11D:
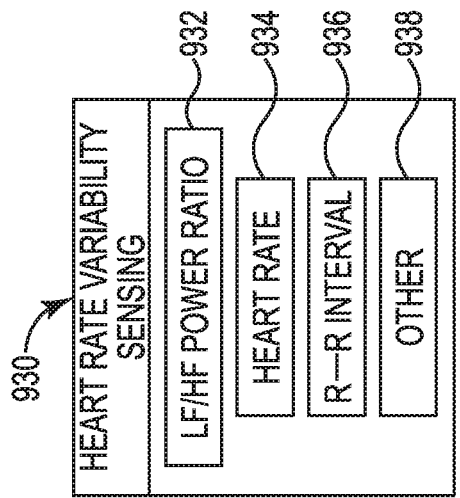
FIG. 11D is a block diagram schematically representing an example heart rate variability (HRV) function.

In some examples, the heart-rate variability may be tracked according to several different frequency bands, such as a very-low frequency (VLF) band, a low frequency (LF) band, and a high frequency (HF) band. In some examples, the very-low frequency (VLF) band may involve frequencies of about 0.005 Hz to about 0.04 Hz, which may correspond to vasomotion and thermoregulation. In some examples, the low frequency (LF) band may involve frequencies of about 0.04 Hz to about 0.15 Hz, which may correspond to sympathetic and parasympathetic activity. In some examples, the low frequency (LF) band may involve frequencies of about 0.15 Hz to about 0.50 Hz, which may correspond to parasympathetic activity and respiration. With this in mind, the heart-rate variability (HRV) parameter 892 may comprise a heart-rate variability sensing function 930 as shown in FIG. 11D, which comprises a LF/HF ratio parameter 932, a heart rate parameter 934, a R—R interval parameter 936, and an other parameter 938.

In some examples, per the LF/HF ration parameter 932, the heart-rate variability sensing function 930 tracks a ratio of low frequency power to high frequency power (a LF/HF ratio) over time, which provides an estimate of sympathovagal balance. A significant decrease in the LF/HF ratio indicates an increase in parasympathetic dominance, which may indicate sleep onset in some examples. For instance, in some examples a decrease of about 25 percent in the LF/HF ratio may be indicative of sleep onset. In some examples, a decrease of about 50 percent in the LF/HF ratio may indicate sleep onset.

In some examples, the heart-rate variability via parameter 892 may provide for secondary confirmation for other features, such as the overall cardiovascular health of the patient.

In some examples, the heart-rate variability per parameter 892 may be used to determine sleep latency, e.g. a length of time to transition from full wakefulness to sleep, such as non-rapid-eye-movement (NREM) sleep. In addition, this heart-rate variability information may be employed to identify sleep onset, i.e. the transition from wakefulness to sleep. For instance, a decrease in heart rate is associated with sleep onset. As further described later in association with at least FIG. 16, this information may enable operation of a stimulation onset parameter 1650.

In some examples, the heart-rate variability per parameter 892 can be employed to distinguish and/or determine sleep stages (including REM), such as in association with sleep stage function 864 (FIG. 11). In some instances, determining sleep stage(s) via HRV parameter 892 may be more accurate than activity-based determinations of sleep stages.

Figure 11E:
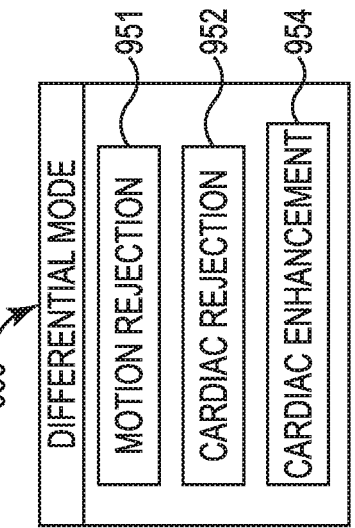
FIG. 11E is a block diagram schematically representing an example differential mode function.
Figure 11B:
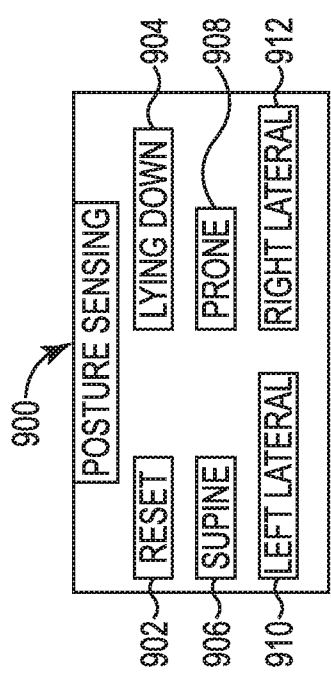
FIG. 11B is a block diagram schematically representing an example posture sending function.
Figure 11C:
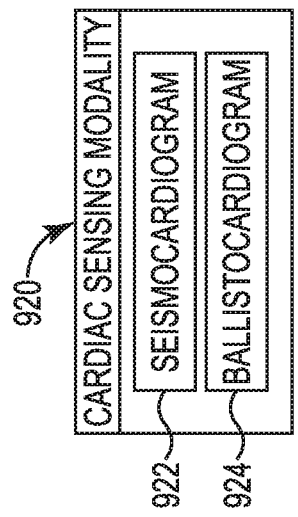
FIG. 11C is a block diagram schematically representing an example cardiac sensing modality function.
Figure 15:
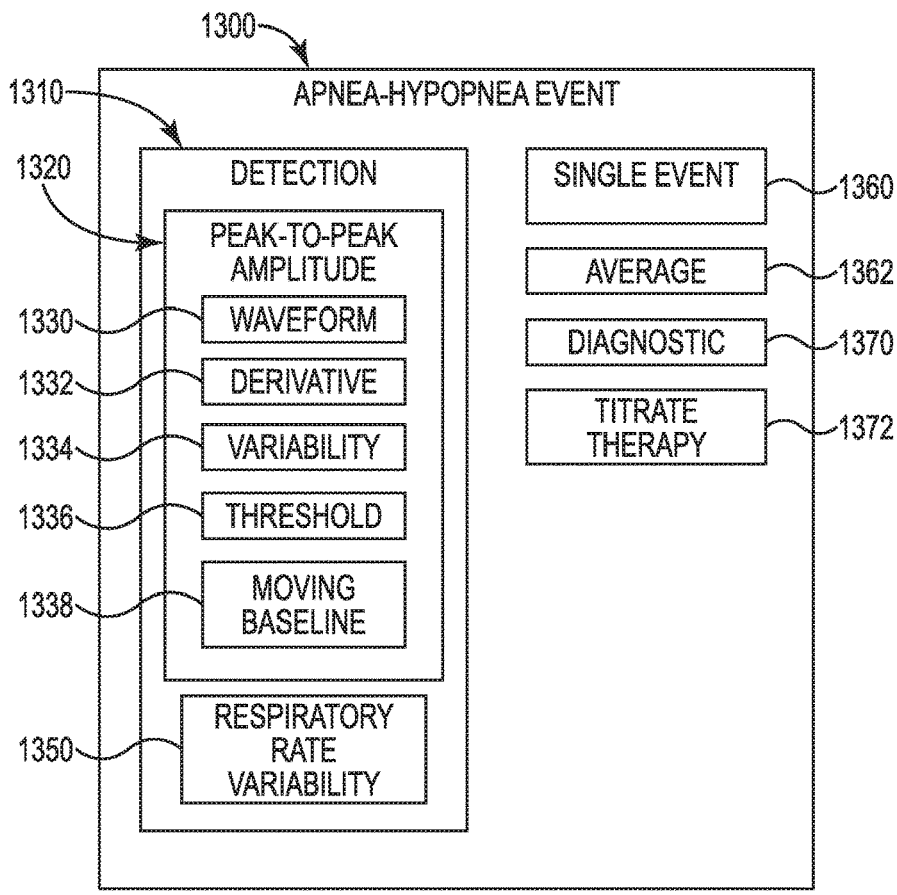
FIG. 15 is a block diagram schematically representing an example apnea-hypopnea event management engine.

In some examples, per heart rate parameter 934 in FIG. 11B, a decrease in heart rate may correspond to sleep onset, which also may be accompanied by an increase in the R—R interval (RRI), which is tracked and/or determined via parameter 936. In some examples, an increase in the R—R interval (RRI) and/or a decrease in variability of a respiratory rate interval (RRI) may be indicative of sleep onset. In some examples, a respiratory rate interval (RRI) is tracked and/or determined via at least respiratory information detection engine 810 (FIG. 11A) and/or respiratory rate variability function 1350 (FIG. 15).

In some examples, the cardiac variability information per parameter 892 may be employed in association with respiratory rate information and/or other information to determine sleep onset, such as further described in association with at least sleep onset parameter 863 and/or stimulation onset parameter 1650.

In some examples, arrhythmias are detected and tracked via parameter 894 with such arrhythmias including, but not limited to, atrial fibrillation.

In some examples, via corroborative parameter 896, the cardiac detection engine 890 can provide a corroboration or secondary confirmation of other features detected and tracked via an accelerometer-based sensor.

Figure 17:
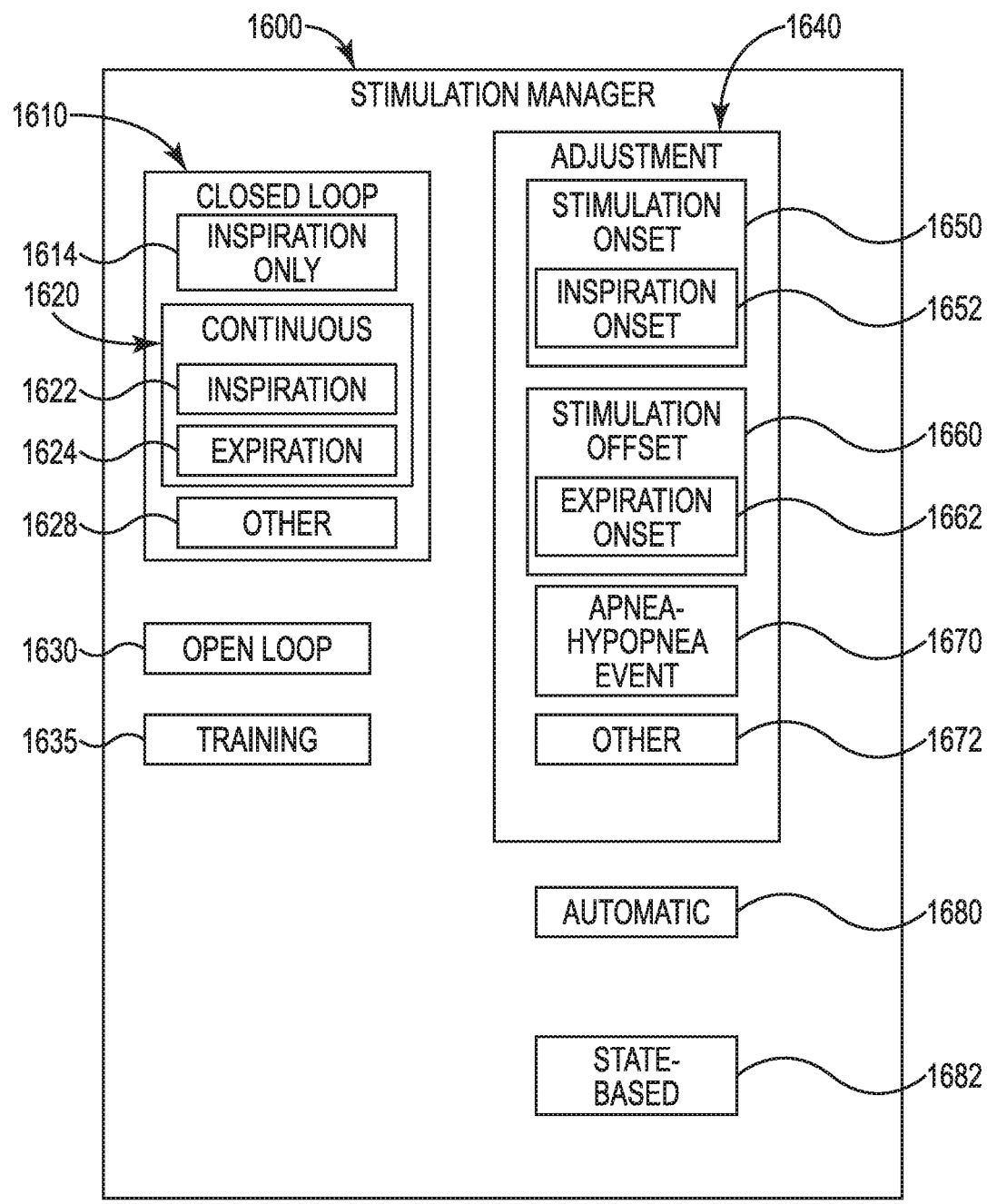
FIG. 17 is a block diagram schematically representing an example stimulation management engine.

In some examples, the accelerometer utilization manager 800 comprises an information vector determination engine 820 to determine an information vector from which neurostimulation therapy parameters can be determined and/or adjusted (such as via stimulation manager 1600 in FIG. 17). In some examples, the information vector is determined according to sensed patient information, which can comprise any combination of the various types of respiratory and non-respiratory information identified via accelerometer utilization management engine 800, and as represented via at least elements 810-890 in FIG. 11A. In some examples, this sensed patient information (from which the information vector is determined) also comprises sensed information from any one of, or combination of, the sensors in sensor type array 1200 in FIG. 13. In some examples, the sensed patient information (from which the information vector is determined) also comprises apnea-hypopnea information as sensed or determined via apnea-hypopnea detection engine 1300 in FIG. 15.

FIG. 11E is a block diagram schematically representing a differential mode engine 950, according to one example of the present disclosure. In some examples, the differential mode engine 950 includes a motion artifact rejection parameter 951, a cardiac rejection parameter 952 and/or a cardiac enhancement parameter 954. In some examples, upon at least two accelerometer sensors being implemented as part of a neurostimulation system (in accordance with the examples of the present disclosure), a differential mode of operation is implemented in which a comparison or combination of the signals from the two different accelerometer sensors takes place. In some examples, a difference between the two signals may be used to reject motion artifacts and/or cardiac artifacts, such as via respective parameters 951, 952. However, in some examples, a difference between the two signals may be used to enhance cardiac or respiratory signals via parameter 954.

FIG. 12A is a block diagram schematically representing a control portion 1000, according to one example of the present disclosure. In some examples, control portion 1000 includes a controller 1002 and a memory 1010. In some examples, control portion 1000 provides one example implementation of a control portion forming a part of, implementing, and/or managing any one of devices, systems, assemblies, circuitry, managers, engines, functions, parameters, sensors, electrodes, and/or methods, as represented throughout the present disclosure in association with FIGS. 1-11B and 13-19.

In general terms, controller 1002 of control portion 1000 comprises at least one processor 1014 and associated memories. The controller 1002 is electrically couplable to, and in communication with, memory 1010 to generate control signals to direct operation of at least some the devices, systems, assemblies, circuitry, managers, engines, functions, parameters, sensors, electrodes, and/or methods, as represented throughout the present disclosure. In some examples, these generated control signals include, but are not limited to, employing manager 1011 stored in memory 1010 to at least manage therapy for sleep disordered breathing and/or manage and operate accelerometer-based sensing in the manner described in at least some examples of the present disclosure. It will be further understood that control portion 1000 (or another control portion) may also be employed to operate general functions of the various therapy devices/systems described throughout the present disclosure.

In response to or based upon commands received via a user interface (e.g. user interface 1036 in FIG. 12C) and/or via machine readable instructions, controller 1002 generates control signals to implement therapy implementation, therapy monitoring, therapy management, and/or management and operation of accelerometer-based sensing in accordance with at least some of the previously described examples of the present disclosure. In some examples, controller 1002 is embodied in a general purpose computing device while in some examples, controller 1002 is incorporated into or associated with at least some of the associated devices, systems, assemblies, circuitry, sensors, electrodes, components of the devices and/or managers, engines, parameters, functions etc. described throughout the present disclosure.

For purposes of this application, in reference to the controller 1002, the term "processor" shall mean a presently developed or future developed processor (or processing resources) that executes sequences of machine readable instructions contained in a memory. In some examples, execution of the sequences of machine readable instructions, such as those provided via memory 1010 of control portion 1000 cause the processor to perform actions, such as operating controller 1002 to implement sleep disordered breathing (SDS) therapy and related management and/or management and operation of accelerometer-based sensing, as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 1010. In some examples, memory 1010 comprises a computer readable tangible medium providing non-volatile storage of the machine readable instructions executable by a process of controller 1002. In other examples, hard wired circuitry may be used in place of or in combination with machine readable instructions to implement the functions described. For example, controller 1002 may be embodied as part of at least one application-specific integrated circuit (ASIC). In at least some examples, the controller 1002 is not limited to any specific combination of hardware circuitry and machine readable instructions, nor limited to any particular source for the machine readable instructions executed by the controller 1002.

FIG. 12B is a diagram 1020 schematically illustrating at least some manners in which the control portion 1000 can be implemented, according to one example of the present disclosure. In some examples, control portion 1000 is entirely implemented within or by an IPG assembly 1025, which has at least some of substantially the same features and attributes as IPG assembly 102 as previously described in association with at least FIGS. 1-11B. In some examples, control portion 100 is entirely implemented within or by a remote control 1030 (e.g. a programmer) external to the patient's body, such as a patient control 1032 and/or a physician control 1034. In some examples, the control portion 1000 is partially implemented in the IPG assembly 1025 and partially implemented in the remote control 1030 (at least one of patient control 1032 and physician control 1034).

In some examples, in association with control portion 1000, user interface (1034 in FIG. 12C) is implemented in remote control 1030.

FIG. 12C is a block diagram schematically representing user interface 1036, according to one example of the present disclosure. In some examples, user interface 1036 forms part or and/or is accessible via a device external to the patient and by which the therapy system may be at least partially controlled and/or monitored. The external device hosting user interface 1036 may be a patient remote (e.g. 1032 in FIG. 11B), a physician remote (e.g. 1034 in FIG. 11B) and/or a clinician portal. In some examples, user interface 1036 comprises a user interface or other display that provides for the simultaneous display, activation, and/or operation of at least some of the various systems, assemblies, circuitry, engines, sensors, components, modules, functions, parameters, as described in association with FIGS. 1-11B and 13-19. In some examples, at least some portions or aspects of the user interface 1036 are provided via a graphical user interface (GUI), and may comprise a display and input.

FIG. 13 is a block diagram schematically representing a sensor type 1100, according to one example of the present disclosure.

As shown in FIG. 13, sensor type array 1200 comprises various types of sensor modalities 1210-1252, any one of which may be used for determining, obtaining, and/or monitoring respiratory information, cardiac information, sleep quality information, sleep disordered breathing-related information, and/or other information related to providing or evaluating patient therapy or general patient well-being.

As shown in FIG. 13, in some examples sensor type 1200 comprises the modalities of pressure 1210, impedance 1212, airflow 1218, radiofrequency (RF) 1230, optical 1214, electromyography (EMG) 1240, electrocardiography (EKG) 1242, ultrasonic 1216, acoustic 1244, and/or other 1250. In some examples, sensor type 1200 comprises a combination 1252 of at least some of the various sensor modalities 1200-1250.

Any one of these sensor modalities, or combinations thereof, may be used in association with, or even independently from, one of the accelerometer sensors previously described in examples of the present disclosure. In some examples, one of the these sensor modalities, or combinations thereof, may be used to corroborate, supplement, and/or evaluate information sensed via one of the accelerometer sensors previously described in examples of the present disclosure.

In some examples, to the extent that at least some of the accelerometer sensors (FIGS. 1-9E) may eliminate or minimize tunneling to place an accelerometer sensor, at least some of the additional sensor modalities in FIG. 13 also may be external sensors or involve minimally invasive sensing implementations, which minimize tunneling or other significant intrusions.

It will be understood that, depending upon the attribute being sensed, in some instances a given sensor modality identified within FIG. 13 may include multiple sensing components while in some instances, a given sensor modality may include a single sensing component. Moreover, in some instances, a given sensor modality identified within FIG. 13 and/or accelerometer sensor (FIGS. 1-9E) may include power circuitry, monitoring circuitry, and/or communication circuitry. However, in some instances a given sensor modality in FIG. 13 or accelerometer sensor (FIGS. 1-9E) may omit some power, monitoring, and/or communication circuitry but may cooperate with such power, monitoring or communication circuitry located elsewhere.

In some examples, a pressure sensor 1210 may sense pressure associated with respiration and can be implemented as an external sensor and/or an implantable sensor. In some instances, such pressures may include an extrapleural pressure, intrapleural pressures, etc. For example, one pressure sensor 1210 may comprise an implantable respiratory sensor, such as that disclosed in Ni et al. U.S. Patent Publication 2011-0152706, published on Jun. 23, 2011, titled METHOD AND APPARATUS FOR SENSING RESPIRATORY PRESSURE IN AN IMPLANTABLE STIMULATION SYSTEM.

In some instances, pressure sensor 1210 may include a respiratory pressure belt worn about the patient's body.

In some examples, pressure sensor 1210 comprises piezoelectric element(s) and may be used to detect sleep disordered breathing (SDB) events (e.g. apnea-hypopnea events), to detect onset of inspiration, and/or detection of an inspiratory rate, etc.

As shown in FIG. 13, in some examples one sensor modality includes air flow sensor 1218, which can be used to sense respiratory information, sleep disordered breathing-related information, sleep quality information, etc. In some instances, air flow sensor 1218 detects a rate or volume of upper respiratory air flow.

As shown in FIG. 13, in some examples one sensor modality includes impedance sensor 1212. In some examples, impedance sensor 1212 may be implemented in some examples via various sensors distributed about the upper body for measuring a bio-impedance signal, whether the sensors are internal and/or external. In some examples, the impedance sensor 1212 senses an impedance indicative of an upper airway collapse.

In some instances, the sensors are positioned about a chest region to measure a trans-thoracic bio-impedance to produce at least a respiratory waveform.

In some instances, at least one sensor involved in measuring bio-impedance can form part of a pulse generator, whether implantable or external. In some instances, at least one sensor involved in measuring bio-impedance can form part of a stimulation element and/or stimulation circuitry. In some instances, at least one sensor forms part of a lead extending between a pulse generator and a stimulation element.

In some examples, impedance sensor 1212 is implemented via a pair of elements on opposite sides of an upper airway.

In some examples, impedance sensor 1212 may take the form of electrical components not formally part of one of the neurostimulation systems described in association with FIGS. 1-9E. For instance, some patients may already have a cardiac therapy device (e.g. pacemaker, defibrillator, etc.) implanted within their bodies, and therefore have some cardiac leads implanted within their body. Accordingly, the cardiac leads may function together or in cooperation with other resistive/electrical elements to provide impedance sensing.

In some examples, whether internal and/or external, impedance sensor(s) 1212 may be used to sense an electrocardiogram (EKG) signal.

In some examples, impedance sensor 1212 is used to detect sleep disordered breathing (SDB) events (e.g. apnea-hypopnea events), to detect onset of inspiration, and/or detection of an inspiratory rate, etc.

In some examples, radiofrequency sensor 1230 shown in FIG. 13 enables non-contact sensing of various physiologic parameters and information, such as but not limited to respiratory information, cardiac information, motion/activity, and/or sleep quality. In some examples, radiofrequency sensor 1230 enables non-contact sensing of other physiologic information. In some examples, radio-frequency (RF) sensor 1230 determines chest motion based on Doppler principles. The sensor 1230 can be located anywhere within the vicinity of the patient, such as various locations within the room (e.g. bedroom) in which the patient is sleeping. In some examples, the sensor 1230 is coupled to a monitoring device to enable data transmission relative to other components of a neurostimulation therapy system (FIGS. 1-9E) and storage in such other components.

In some examples, one sensor modality may comprise an optical sensor 1214 as shown in FIG. 13. In some instances, optical sensor 1214 may be an implantable sensor and/or external sensor. For instance, one implementation of an optical sensor 1214 comprises an external optical sensor for sensing heart rate and/or oxygen saturation via pulse oximetry. In some instances, the optical sensor 1214 enables measuring oxygen desaturation index (ODI). In some examples, the optical sensor 1214 comprises an external sensor removably couplable on the finger of the patient.

In some examples, optical sensor 1214 can be used to measure ambient light in the patient's sleep environment, thereby enabling an evaluation of the effectiveness of the patient's sleep hygiene and/or sleeping patterns.

As shown in FIG. 13, in some examples one sensor modality comprises EMG sensor 1240, which records and evaluates electrical activity produced by muscles, whether the muscles are activated electrically or neurologically. In some instances, the EMG sensor 1240 is used to sense respiratory information, such as but not limited to, respiratory rate, apnea events, hypopnea events, whether the apnea is obstructive or central in origin, etc. For instance, central apneas may show no respiratory EMG effort.

In some instances, the EMG sensor 1240 may comprise a surface EMG sensor while, in some instances, the EMG sensor 1240 may comprise an intramuscular sensor. In some instances, at least a portion of the EMG sensor 1240 is implantable within the patient's body and therefore remains available for performing electromyography on a long term basis.

In some examples, one sensor modality may comprise EKG sensor 1242 which produces an electrocardiogram (EKG) signal. In some instances, the EKG sensor 1242 comprises a plurality of electrodes distributable about a chest region of the patient and from which the EKG signal is obtainable. In some instances, a dedicated EKG sensor(s) 1242 is not employed, but other sensors such as an array of bio-impedance sensors 1212 are employed to obtain an EKG signal. In some instances, a dedicated EKG sensor(s) is not employed but EKG information is derived from a respiratory waveform, which may be obtained via any one or several of the sensor modalities in sensor type array 1200 of FIG. 13. In some examples, EKG sensor 1242 is embodied or at least implemented in part as at least one of the accelerometer sensors (FIGS. 1-9E)

In some examples, an EKG signal obtained via EKG sensor 1242 may be combined with respiratory sensing (via pressure sensor 1210, impedance sensor 1212, and/or an accelerometer sensor) to determine minute ventilation, as well as a rate and phase of respiration. In some examples, the EKG sensor 1242 may be exploited to obtain respiratory information.

In some examples, EKG sensor 1242 is used to detect sleep disordered breathing (SDB) events (e.g. apnea-hypopnea events), to detect onset of inspiration, and/or detection of an inspiratory rate, etc.

As shown in FIG. 13, in some examples one sensor modality includes an ultrasonic sensor 1216. In some instances, ultrasonic sensor 1216 is locatable in close proximity to an opening (e.g. nose, mouth) of the patient's upper airway and via ultrasonic signal detection and processing, may sense exhaled air to enable determining respiratory information, sleep quality information, sleep disordered breathing information, etc. In some instances, ultrasonic sensor 1216 may comprise at least some of substantially the same features and attributes as described in association with at least Arlotto et al. PCT Published Patent Application 2015-014915 published on Feb. 5, 2015.

In some examples, acoustic sensor 1244 comprises piezoelectric element(s), which sense acoustic vibration. In some implementations, such acoustic vibratory sensing may be used to detect sleep disordered breathing (SDB) events (e.g. apnea-hypopnea events), to detect onset of inspiration, and/or detection of an inspiratory rate, etc. In some examples, acoustic sensor 1244 is implemented via one of the accelerometer sensors in the examples of the present disclosure as previously described in association with at least acoustic engine 850 in FIG. 11A. In some examples, a therapy system can comprise at least two acoustic sensors, such as a first acoustic sensor implemented via an accelerometer sensor (FIGS. 1-9E) and a second acoustic sensor implemented via another type of acoustic sensing (e.g. piezoelectric).

In some examples, acoustic sensor 1244 detects snoring information, which may be used in detection, evaluation, and/or modification of sleep-related information and/or therapy parameters.

In some examples, one of the sensor types 1200 or a combination of such sensors senses local or gross motion, such as snoring, inspiration/expiration, etc., which may be indicative to sleep quality, sleep disordered breathing events, general respiratory information, etc.

In some examples, information sensed via one of the sensors in FIG. 13, such as but not limited to motion information, can be used in a training mode of an implantable neurostimulation system (as described herein) to correlate the patient's respiration with the sensed motion. In some examples, this training occurs in cooperation with training mode 1635, which is later described in association with FIG. 17.

In some examples, several sensor modalities of the sensory type array 1200 are combined, as represented via combination identifier 1252.

FIG. 14 is a block diagram schematically representing accelerometer operation engine 1280, according to one example of the present disclosure. As shown in FIG. 14, in some examples accelerometer operation engine 1280 comprises a feature extraction function 1290 and a power management function 1296. In general terms, the feature extraction function 1290 determines which features to extract from the different axis signals and/or meta-vectors (e.g. combined axis signals). In some examples, such feature extraction is implemented via a power spectral density parameter 1292 and a frequency threshold parameter 1294. For instance, a cardiac-related information obtained via an accelerometer sensor, such as via engine 890 in FIG. 11A, can have a different signature (e.g. recognizable waveform characteristics) than respiration-related information. In some examples, via parameter 1292 some such cardiac signals can be classified as having a dominant power spectral density meeting or exceeding a frequency threshold (as set via parameter 1294) while respiratory signals can be classified as having a dominant power spectral density which falls below the same frequency threshold. Stated differently, the power spectral density parameter 1292 facilitates identifying sensed cardiac information as a first portion of the sensed accelerometer signals which exhibit substantial power at relatively higher frequencies and identifying sensed respiratory information as a second portion of the sensed accelerometer signals which exhibit substantial power at relative lower frequencies.

Upon differentiating cardiac information and respiratory information from sensed accelerometer signals, the various devices, managers, engines, functions, parameters as described throughout examples of the present disclosure may be employed to determine other physiologic information, which may or may not relate to detecting, evaluating, diagnosing, and/or treating sleep disordered breathing behavior.

In some examples, the power management function 1296 provides for managing power used for sensing. In some instances, via function 1296 a higher sampling rate can be used at an accelerometer sensor (FIGS. 1-9E) when SDB events are detected while a lower sampling rage can be used during normal respiration. In some instances, power is not supplied (or greatly reduced) to an accelerometer sensor when stimulation is delivered via an open loop mode (1630 in FIG. 17).

In some examples, the power management function 1296 is associated with at least one sensing element of a SDB care device to selectively activate and/or de-activate at least one function of the at least one sensing element at selective periods of time based on information sensed via the at least one sensor. In some examples, the sensed information comprises posture information. In some examples, the posture information comprises changes in posture and/or a lack of change in posture. In some examples, the sensed information comprises cardiac information or other information which is in addition to or instead of the posture information. In some examples, the at least one function of the at least one sensor comprises a posture detection or tracking function (e.g. position tracking). As just one of many examples, the power management function 1296 may deactivate posture detection after detecting a generally vertical posture and activate posture detection upon sensed respiratory information (e.g. respiratory variability) determines sleep. Of course, in some examples the at least one function which is selectively activated or de-activated may comprise a function other than posture or in addition to posture, such as any one or more of the various functions and modalities described in association with at least FIGS. 11A-17.

In some examples, the at least one sensing element governed via the power management function 1296 comprises an accelerometer-based sensor. In some examples, the at least one sensing element governed via the power management function 1296 includes other sensing modalities instead of an accelerometer-based sensor or in addition to an accelerometer-based sensor.

FIG. 15 is a block diagram schematically representing an apnea-hypopnea event management engine 1300, according to one example of the present disclosure. As shown in FIG. 15, in some examples the management engine 1300 comprises a detection engine 1310, which includes a peak-to-peak amplitude function 1320 and a respiratory rate variability function 1350.

In general terms, the detection engine 1310 may detect apnea-hypopnea events based on information sensed via at least an accelerometer-based sensor (FIGS. 1-9E) in accordance with at least some examples of the present disclosure. For instance, in some examples an apnea-hypopnea event management engine 1300 may track a number of apnea-hypopnea events based on at least one of changes in respiratory amplitude, changes in respiratory rate, and/or changes in heart rate, at least some of which are further described below and elsewhere throughout the present disclosure. In some examples, the apnea-hypopnea event management engine 1300 may track a number of apnea-hypopnea events in association with different sleep stages, which facilitate correlating the occurrence of such events relative to particular sleep stages. In some examples, upon at least some changes in a number of apnea-hypopnea events, the apnea-hypopnea event management engine 1300 is to automatically implement changes to stimulation therapy via a pulse generator. In some examples, the apnea-hypopnea event management engine 1300 may sometimes be referred to as an apnea-hypopnea event function.

In some examples, the peak-to-peak amplitude function 1320 can detect an apnea-hypopnea event (e.g. SDB event) per waveform parameter 1330 upon a peak-to-peak amplitude of a respiratory waveform falling below a threshold (set via threshold parameter 1336) or upon such a peak-to-peak amplitude falling below a moving baseline (set via parameter 1338). In some examples, the peak-to-peak amplitude function 1320 can detect an apnea-hypopnea event (e.g. SDB event) per derivative parameter 1332 upon a peak-to-peak amplitude of a derivative of a respiratory waveform falling below a threshold (set via threshold parameter 1336) or upon such a peak-to-peak amplitude of a derivative of a respiratory waveform falling below a moving baseline (set via parameter 1338).

In some examples, the peak-to-peak amplitude function 1320 can detect an apnea-hypopnea event (e.g. SDB event) per variability parameter 1334 upon a peak-to-peak amplitude of a respiratory waveform having a variability greater than a threshold (set via threshold parameter 1336).

In some examples, the respiratory rate function 1350 can detect an apnea-hypopnea event (e.g. SDB event) upon a sensed respiratory rate having a variability greater than a threshold (set via threshold parameter 1336). In some examples, the detection engine 1310 may also detect apnea-hypopnea events based on information sensed via sensors in addition to, or in combination with, an accelerometer sensor (in accordance with at least some examples of the present disclosure). In some examples, such additional sensors can be one of the sensor type modalities 1100 described in association with at least FIG. 13.

In some examples, apnea-hypopnea event management engine 1300 comprises a single event function 1360, which can detect a single apnea hypopnea event. In some examples, apnea-hypopnea event management engine 1300 comprises an average function 1362 to detect and/or track an average number of apnea-hypopnea events over time. In some instances, such averages can be expressed as severity index, which in some examples comprises an apnea-hypopnea index (AHI).

In some examples, apnea-hypopnea event management engine 1300 comprises a diagnostic function 1370 to use apnea-hypopnea detection information for diagnosing patient conditions, including but not limited to obstructive sleep apnea, while therapy titration function 1372 can use apnea-detection information to enable titrating stimulation therapy for obstructive sleep apnea.

FIG. 16 is a block diagram schematically representing a posture information engine 1400, according to one example of the present disclosure. As previously noted, in at least some instances, the posture may sometimes be referred to as body position. As shown in FIG. 16, in some examples posture information engine 1400 comprises a calibration function 1410 to compensate for an unknown orientation of the accelerometer as mounted within the patient's body. In some examples, an automatic parameter 1412 performs such calibration automatically, such as when the patient is walking because such behavior is consistent with a gravity vector pointing downward. In some examples, a manual parameter 1414 can be used to perform calibration, such as via measuring a gravity vector in at least two known patient orientations, of the accelerometer orientation.

In some examples, posture information engine 1400 comprises a position tracking function 1420 to track physiologic information in association with at least some respective different postures. In some examples, the physiologic information comprises an amount of time spent sleeping in each posture. In some instances, such tracked physiologic information may include a number of switches between different postures. In some examples, such tracked physiologic information may include a lack of changes between different postures. In some examples, posture information engine 1400 comprises an apnea-hypopnea events function 1430 to track a number of apnea-hypopnea events that occurs in each respective posture. In some examples, the tracking of the number of apnea-hypopnea events may occur in association with sensed respiratory information which may be obtained via an accelerometer-based sensor and/or other respiratory information sensing modalities.

Via this arrangement, in some examples sleep position (e.g. left side, right side, supine, prone, etc.) may be used to determine the effectiveness of SDB therapy according to sleep position, and in some instances, the SDB therapy may be automatically adjusted based on the orientation (i.e. sleep position) of the patient.

In some examples, upon determining at least some changes between multiple different postures via position tracking function 1420 (and/or posture function 840 in FIG. 11A, 900 in FIG. 11B), changes are automatically implemented in stimulation therapy via a pulse generator.

In some instances, this information regarding sleep position (obtained via a sensed posture information) may be communicated via a notification function 1440 to the patient during a sleep period in order to induce the patient to change their sleep position into one more conducive to efficacious therapy. In some examples, the communication via notification function 1440 may occur by an audible notification 1442 or haptic notification 1444 (e.g. vibratory, motion, etc.) implemented via wireless communication to a patient remote (e.g. 1030 in FIG. 12B), a user interface (e.g. 1034 in FIG. 12C), a patient support (e.g. 794 in FIG. 9C). In some examples, the haptic notification 1444 may be communicated via direct muscle stimulation via wireless communication to a wearable muscle stimulation device.

Among other uses, the sensed posture information may be employed by a clinician to adjust stimulation therapy and/or employed by a therapy device (and/or manager such as 1600 in FIG. 17) to automatically adjust stimulation therapy to cause a decrease in the moving average of the sleep apnea index (e.g. AHI). Moreover, in some examples, this information may be used to communicate to the patient via audio or non-audio techniques to change their sleep position to a position (e.g. left side) more amenable to regular respiration.

FIG. 17 is a block diagram schematically representing a stimulation manager 1600, according to one example of the present disclosure.

While not necessarily expressly stated directly in association with each aspect of the example represented by FIG. 17, it will be understood that stimulation manager 1600 may utilize and/or coordinate with at least some of the therapy-related features, engines, functions, parameters, etc. as described throughout at least some examples of the present disclosure.

As shown in FIG. 17, in some examples, stimulation manager 1600 includes a closed loop mode engine 1610, an open loop mode engine 1630, a training engine 1635, and an adjustment engine 1640.

In some examples, once therapy is initiated during a daily treatment period, stimulation is performed generally continuously. In some examples, once therapy is initiated during a daily sleep period, stimulation is performed on an "as-needed" basis, such that stimulation occurs when needed but is otherwise suspended.

In general terms, stimulation is applied via general parameters, such as on/off, amplitude, rate, width, duty cycle of burst, start of burst, electrode configuration, ramping of stimulation amplitude, etc. In some examples, via adjustment engine 1640, stimulation intensity is adjusted according to at least one or a combination of parameters, such as but not limited to, a pulse amplitude, number of pulses, pulse width, burst time, and/or electrode configuration.

In some examples, transitioning between different electrode configurations may be implemented via pulse interleaving. However, in some examples, transitioning between different electrode configurations may be implemented without pulse interleaving.

In some examples, the closed loop mode engine 1610 causes a neurostimulation system to apply therapeutic stimulation, at least in part, based on received and/or sensed physiologic information related to the intended therapy. As shown in FIG. 17, in some examples the closed loop mode engine 1610 includes an inspiration only function 1614, a continuous function 1620, and an other function 1628.

In some examples, via the inspiration only function 1614, stimulation is delivered during only the inspiratory phase of a respiratory cycle. Among other features, this arrangement may minimize muscle fatigue and/or reduce energy usage by the stimulation system, thereby potentially prolonging longevity of a power source.

In some examples, via the continuous function 1620, stimulation is delivered continuously during a treatment period. Stated differently, the stimulation is applied throughout the entirety of each respiratory cycle occurring within the treatment period such that the stimulation is not synchronized to occur solely with inspiration or another defined fraction of a respiratory cycle.

In some examples, the configurable stimulation parameters (e.g. amplitude, rate, width, etc.) are implemented according to one set of values to coincide with each inspiratory phase (per inspiration parameter 1622) while a different set of values (for at least some of the same configurable stimulation parameters) are implemented to coincide with each expiratory phase per expiration parameter 1624. In this arrangement, the sensed respiratory information can be used to determine an appropriate value of the configurable parameters for each phase and/or detect the beginning, midpoint, end, etc. of each respective phase and expiratory pause.

In some examples, the other function 1628 can enable implementing custom stimulation protocols that operate in a closed loop mode in which different levels and stimulation schemes can be implemented during different portions of a respiratory cycle.

In some examples, the open loop mode function 1630 causes a neurostimulation system to apply therapeutic stimulation that is not in response to receiving and/or sensing physiologic information, such as but not limited to respiration information. In such examples, once a treatment period is initiated, stimulation will be delivered without regard to inspiratory and/or expiratory phases. The stimulation may or may not be continuous. However, it will be understood that received or sensed respiratory information (or other related information) may still be used to track the patient's health, evaluate therapy, etc. In some examples, open loop mode function 1630 incorporates a stimulation period and duty cycle such that stimulation occurs during at least a majority of any given inspiratory phase.

In some examples, as shown in FIG. 17, an adjustment engine 1640 of stimulation manager 1600 includes a stimulation onset parameter 1650, a stimulation offset parameter 1660, an apnea-hypopnea event parameter 1670, and a posture parameter 1672. The stimulation onset parameter 1650 enables adjusting stimulation parameters and/or other therapy parameters in relation to inspiration onset 1652, such as but not limited to, a configurable delay before the onset of inspiration. In some instances, a prediction is based on previous inspiration onset times.

In some examples, via stimulation onset parameter 1650, stimulation is initiated when start-of-sleep (i.e. sleep onset) is detected. In some examples, start-of-sleep may be determined in accordance with a start-of-sleep parameter 863, such as previously described in association with at least FIG. 11A. For example, in some examples a determination of sleep onset may involve analyzing a R—R interval from a cardiac waveform to identify decreases in a LF/HF power ratio, R—R interval increases, and/or R—R variability, as well as observing decreases in respiratory rate variability (RRV). In some examples, this cardiac variability information is used in combination with activity information (842 in FIG. 11A), posture information (840 in FIG. 11A; 1400 in FIG. 16), and/or respiratory information to determine sleep onset, as well as sleep offset, i.e. termination of sleep.

In some examples, the same parameters used to determine sleep onset also may be used to determine end sleep 865 (i.e. sleep offset or termination of sleep). In some examples, a determination of sleep termination may thereby triggers terminating stimulation per stimulation offset parameter 1660.

In some examples, activity information (e.g. 842 in FIG. 11A) and/or respiratory information sensed via at least one sensing element of a SDB care device may at least partially determine sleep onset and/or sleep termination.

In some examples, the stimulation offset parameter 1660 enables adjusting stimulation parameters and/or other therapy parameters in relation to expiration onset 1662, such as but not limited to, a configurable delay after the onset of expiration. In some instances, a prediction is based on previous expiration onset times. In some instances, the stimulation offset can be set as a fixed time after the onset of inspiration.

In some examples, the apnea-hypopnea event parameter 1670 enables adjusting stimulation settings in relation to detection of apnea-hypopnea events in which the adjusted stimulation parameters remain within clinician-configurable limits. In one instance, to the extent that a lesser number of apnea-hypopnea events are detected relative to a threshold, one can reduce the intensity of stimulation according to at least one stimulation parameter (e.g. amplitude, rate, pulse width, etc. as noted above), thereby conserving energy and minimizing unnecessary nerve stimulation, which in turn reduces muscle fatigue.

In some examples, the posture parameter 1672 enables adjusting stimulation settings in relation to different postures (e.g. supine position, prone position, left side position, right side position). In one aspect, the stimulation settings are configurable such that a different set of stimulation settings may be applied to each different posture. Accordingly, as a patient moves into different postures throughout the night (during a treatment period), the stimulation settings can be automatically adjusted. In some examples, via the posture parameter 1672 these configurable stimulation settings are adjusted for each patient.

In some examples, when standing or sitting upright is detected via an accelerometer sensor (FIGS. 1-9E) and/or other sensors, the posture parameter 1672 can reduce stimulation to a minimal level or terminate stimulation completely.

In some examples, posture function 1672 may operate in coordination with posture function 840 (FIG. 11A) and/or posture information engine 1400 (FIG. 16).

In some examples, upon detecting motion artifacts (see engine 870 in FIG. 11A), the adjustment engine 1640 may implement the open loop function 1630 (FIG. 17) to ensure sufficient stimulation for at least a period of time during which the motion artifacts are present.

In some examples, as shown in FIG. 17, the stimulation manager 1600 comprises a training engine 1635, which calibrates stimulation parameters and sensed information parameters relative to sensed parameters of a sleep study, such as a polysomnography (PSG) study. In some instances, such training utilizes the external instruments available in a PSG study to provide reference signals for respiration and apnea-hypopnea event detection.

In some examples, via an automatic stimulation function 1680, stimulation is enabled and disabled (e.g. turned on and off) automatically according to various parameters. In some examples, such parameters include posture, respiratory rate, apnea-hypopnea event count, etc. However, in some examples, because sleep disordered breathing is generally associated with sleep periods of the patient, in some examples a treatment period automatically coincides with a daily sleep period of the patient such that the automatic stimulation state function 1680 enables/disables stimulation according to the above-identified parameters. In some instances, the daily sleep period is identified via sensing technology which detects motion, activity, posture of the patient, as well as other indicia, such as heart rate, breathing patterns, etc. However, in some instances, the daily sleep period is selectably preset, such from 10 pm to 6 am or other suitable times.

In some examples, as shown in FIG. 17, stimulation manager 1600 comprises a state-based operation engine 1682 to cause different states of operation for stimulation therapy. In some examples, the engine 1682 includes operation of an inversion detection state to deliver stimulation with a fixed rate and fixed duty cycle per open loop engine 1630, such as in cooperation with inversion detection engine 830 in FIG. 11A. In some examples, the inversion detection state may be entered upon occurrence of a "reset", which may occur upon a change in posture, a motion artifact above a threshold, and/or the occurrence of respiratory rate variability above a threshold. On detection of stable posture, motion artifact below a threshold, and/or respiratory rate variability below a threshold for a configurable duration, in some examples, the engine 866 includes transition to a closed-loop state in which stimulation is delivered per closed loop engine 1610 until a "reset" occurs. In some examples, in the closed-loop state the respiration signal can be inverted prior to further processing based on the determination of inversion detection engine 830. In this way, efficacious stimulation can be delivered in the presence of sensor noise (including but not limited to motion artifact) and/or unstable respiration (including apnea and/or hypopnea events) by virtue of open-loop stimulation engine 1630. In some examples, the state-based operation engine 1682 includes additional states of operation, such as at least some of the various states, modes, and/or adjustments of stimulation manager 1600.

Figure 18:
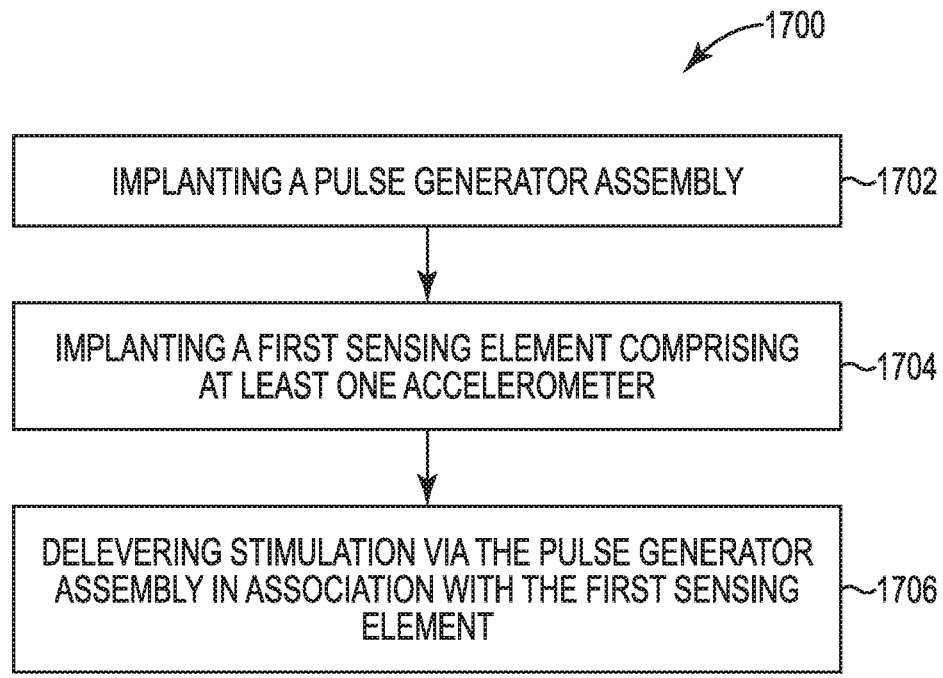
FIGS. 18-19 are each a flow diagram schematically representing an example method of stimulation therapy.

FIG. 18 is a flow diagram schematically representing a method 1700 of neurostimulation therapy, according to one example of the present disclosure. In some examples, method 1700 can be performed according to at least some of the devices, systems, assemblies, components, sensors, electrodes, managers, engines, functions, and/or parameters, as previously described in association with FIGS. 1-17. In some examples, method 1700 can be performed via at least some devices, systems, assemblies, components, sensors, electrodes, managers, engines, functions, and/or parameters other than those previously described in association with FIGS. 1-17.

As shown in FIG. 18, at 1702 method 1700 comprises implanting a pulse generator assembly, and at 1704, implanting a first sensing element comprising an accelerometer-based sensor. At 1706, method 1700 comprises delivering stimulation via the pulse generator assembly in association with the first sensing element.

Figure 19:
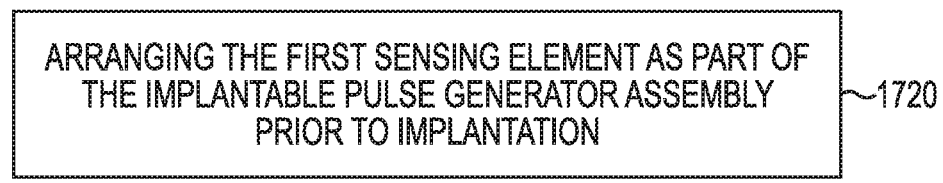

As shown in FIG. 19, in some examples, method 1700 further comprises arranging the first sensing element as part of the implantable pulse generator assembly prior to implantation.

Figure 20:
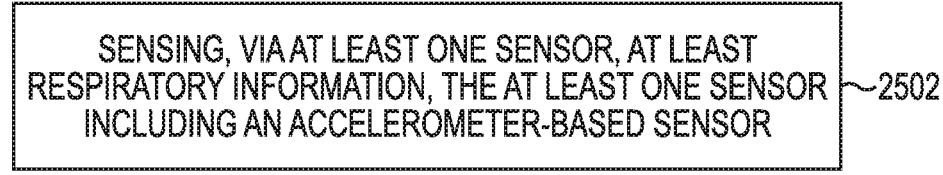
FIG. 20 is a flow diagram schematically representing an example method.

FIG. 20 is a flow diagram schematically representing a method 2500, according to one example of the present disclosure. In some examples, method 2500 can be performed according to at least some of the devices, systems, assemblies, components, sensors, electrodes, managers, engines, functions, and/or parameters, as previously described in association with FIGS. 1-17. In some examples, method 2500 can be performed via at least some devices, systems, assemblies, components, sensors, electrodes, managers, engines, functions, and/or parameters other than those previously described in association with FIGS. 1-17.

In some examples, as shown at 2502 in FIG. 20 method 2500 of sleep disordered breathing care comprises sensing, via at least one sensor, at least respiratory information, wherein the at least one sensor comprises an accelerometer-based sensor. In some examples, method 2500 also comprises implanting the at least one sensor.

In some examples, method 2500 comprises selectively activating or deactivating, via a power management function, at least one function of the at least one sensor at selective periods of time based on information sensed via the at least one sensor, wherein the sensed information comprises posture information.

In some examples, method 2500 comprises determining, via a posture function associated with the at least one sensor, posture information to indicate a respective one of multiple different postures.

In some examples, method 2500 comprises the multiple different postures comprising a generally vertical position and a lying down position, and the lying down position comprising at least one of a supine position, a prone position, a left lateral decubitus position, and a right lateral decubitus position.

In some examples, method 2500 comprises, upon determining at least some changes between multiple different postures, automatically implementing via the posture function changes to stimulation therapy via a pulse generator.

In some examples, method 2500 comprises tracking physiologic information, via a position tracking parameter of the posture function, in association with at least some postures.

In some examples, method 2500 comprises the tracked physiologic information, including the respiratory information, comprising a number of apnea-hypopnea events for each posture.

In some examples, method 2500 comprises tracking a number of apnea-hypopnea events based on at least one of changes in respiratory amplitude, changes in respiratory rate, and changes in heart rate.

In some examples, method 2500 comprises, wherein upon at least some changes in a number of apnea-hypopnea events, automatically implementing changes to stimulation therapy via a pulse generator.

In some examples, method 2500 comprises determining via a respiration monitor associated with the at least one sensor, at least one of an inspiratory phase and an expiratory phase, based on respiration information including at least one of: respiratory period information; and respiratory phase information.

In some examples, method 2500 comprises selectively stimulating, via a pulse generator, an upper airway patency-related nerve via a stimulation element, during a portion of the inspiratory phase, based on respiration information from the respiration monitor.

In some examples, method 2500 comprises arranging a pulse generator to include the at least one sensor.

In some examples, method 2500 comprises stimulating, via a pulse generator, stimulate an upper airway patency-related nerve independent of the respiration information.

In some examples, method 2500 comprises wherein, in addition to the accelerometer-based sensor, the at least one sensor comprises a respiratory sensor to detect at least some of the respiratory information.

In some examples, method 2500 comprises determining, via at least one of sensed activity information and sensed respiratory information, at least one of sleep onset and sleep termination.

In some examples, method 2500 comprises determining, via cardiac information sensed via at least partially via the at least one sensor, at least one of sleep onset and sleep termination according to at least one of: heart rate variability (HRV) information; and heart rate information.

In some examples, method 2500 comprises selectively stimulating, via a pulse generator, an upper airway patency-related nerve via a stimulation element, wherein the pulse generator enables stimulation upon a determination of sleep onset and disables stimulation upon a determination of sleep termination.

In some examples, method 2500 comprises selectively stimulating, via a pulse generator, an upper airway patency-related nerve via a stimulation element, wherein the pulse generator enables stimulation upon a determination of sleep onset and disables stimulation upon a determination of sleep termination.

In some examples, method 2500 comprises determining, at least partially via the at least one sensor, cardiac information including at least one of heart rate variability (HRV) information; and heart rate information.

In some examples, method 2500 comprises determining, at least partially via the at least one sensor, respiration information including at least one of respiratory rate variability (RRV) information and respiratory rate information.

In some examples, method 2500 comprises electively deactivating at least one operation of the at least one sensor at selective periods of time in relation to the cardiac information.

In some examples, method 2500 comprises determining, at least partially via the at least one sensor, at least some sleep stages based on at least one of: activity information; posture information; respiratory rate information; respiratory rate variability (RRV) information; heart rate variability (HRV) information; and heart rate information.

In some examples, method 2500 comprises detecting a number of apnea-hypopnea events in association with at least some of the respective sleep stages.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

The invention claimed is:

1. A sleep disordered breathing (SDB) care device comprising:
   at least one implantable accelerometer sensor to sense physiologic information; and
   a control portion to receive the sensed physiologic information from the implantable accelerometer sensor, wherein the control portion comprises:
      a feature extraction function to differentiate within the sensed physiologic information from the implantable accelerometer sensor, according to power spectral density, respiratory information from cardiac information; and
      a respiration monitor to determine, at least one of an inspiratory phase and an expiratory phase, based on the sensed respiratory information.

2. The SDB care device of claim 1, wherein the control portion comprises a power management function to selectively activate or de-activate at least one function of the implantable accelerometer sensor at selective periods of time based on the sensed physiologic information, wherein the sensed physiologic information comprises posture information.

3. The SDB care device of claim 1, wherein the control portion is to receive the sensed physiologic information, including posture information, and wherein the control portion comprises a posture function to determine, based on the sensed posture information, an indication of a respective one of multiple different postures, including a generally vertical position and a lying down position, and wherein the lying down position comprises at least one of a supine position, a prone position, a left lateral decubitus position, and a right lateral decubitus position.

4. The SDB care device of claim 3, wherein the posture function of the control portion is to automatically implement, upon determination from the sensed posture information of changes between the multiple different postures, changes to a stimulation therapy signal via the control portion.

5. The SDB care device of claim 3, wherein the posture function of the control portion comprises a position tracking parameter to track the sensed physiologic information in association with at least some of the multiple different postures.

6. The SDB care device of claim 5, wherein, via the position tracking parameter, the posture function of the control portion is to track the sensed physiologic information as including the sensed respiratory information, which comprises tracking a number of apnea-hypopnea events for each respective multiple different posture determined from the sensed posture information.

7. The SDB care device of claim 1, wherein the control portion comprises an apnea-hypopnea event function to track a number of apnea-hypopnea events based on the sensed respiratory information and the sensed cardiac information according to at least one of:
   changes in respiratory amplitude,
   changes in respiratory rate; and
   changes in heart rate.

8. The SDB care device of claim 7, wherein the apnea-hypopnea event function of the control portion, is to automatically implement, upon tracking changes in a number of apnea-hypopnea events, changes to a stimulation therapy signal via the control portion.

9. The SDB care device of claim 1, wherein the sensed respiratory information comprises at least one of:
   respiratory period information; and
   respiratory phase information.

10. The SDB care device of claim 1, comprising:
    an implantable pulse generator to generate a stimulation signal to selectively stimulate an upper airway patency-related nerve via a stimulation element, during a portion of the inspiratory phase, based on the sensed respiratory information from the respiration monitor of the control portion.

11. The SDB care device of claim 10,
    wherein the implantable pulse generator houses the implantable accelerometer sensor and the control portion.

12. The SDB care device of claim 1, further comprising an implantable respiratory sensor, in addition to the implantable accelerometer sensor, to detect at least some of the sensed respiratory information.

13. The SDB care device of claim 1, wherein the implantable accelerometer sensor is to sense activity information, and wherein the control portion to receive the sensed activity information, and wherein the control portion comprises an activity function and the respiratory monitor to determine, via at least one of the sensed activity information and the sensed respiratory information respectively, at least one of sleep onset and sleep termination.

14. The SDB care device of claim 13, wherein the control portion comprises:
    a cardiac information function to determine, at least partially via the sensed cardiac information, the sensed activity information, and the sensed respiratory information, at least one of sleep onset and sleep termination according to heart rate variability (HRV) information.

15. The SDB care device of claim 14, comprising:
    an implantable pulse generator, which houses the control portion and which is to generate a stimulation signal to selectively stimulate an upper airway patency-related nerve via a stimulation element, wherein the implantable pulse generator is to deliver the stimulation signal upon the determination of sleep onset by the cardiac information function of the control portion and is to disable the stimulation signal upon the determination of sleep termination by the cardiac information function of the control portion.

16. The SDB care device of claim 13,
    an implantable pulse generator, which houses the control portion, and which is to generate a stimulation signal to selectively stimulate an upper airway patency-related nerve via a stimulation element, wherein the implantable pulse generator is to deliver the stimulation signal upon a determination of sleep onset and is to disable the stimulation signal upon a determination of sleep termination.

17. The SDB care device of claim 1, wherein the control portion comprises a cardiac information function to determine, at least partially based on the sensed cardiac information, at least one of:
heart rate variability (HRV) information; and
heart rate information.

18. The SDB care device of claim 17,
wherein the respiratory monitor is to determine, based on the sensed respiratory information, at least one of:
respiratory rate variability (RRV) information; and
respiratory rate information.

19. The SDB care device of claim 1, wherein the implantable accelerometer sensor is to sense, in addition to the sensed respiratory information and sensed cardiac information, at least one of activity information and posture information, and comprising:
a control portion comprising a sleep function to determine, sleep stages via at least one of:
the sensed activity information;
the sensed posture information;
respiratory rate information from the sensed respiratory information;
respiratory rate variability (RRV) information from the sensed respiratory information;
heart rate variability (HRV) information from the sensed cardiac information; and
heart rate information from the sensed cardiac information.

20. The SDB care device of claim 19, wherein the control portion comprises:
an apnea-hypopnea event engine to detect, based on at least some of the sensed respiratory information, a number of apnea-hypopnea events in association with at least some of the determined respective sleep stages.

21. A sleep disordered breathing (SDB) care device, comprising:
an implantable accelerometer sensor to sense respiratory information;
an implantable pulse generator to generate a stimulation signal to stimulate, via a stimulation element and in an open loop mode without regard to respiratory phase information of the sensed respiratory information, an upper airway patency-related nerve, wherein the implantable pulse generator comprises a control portion, wherein the control portion comprises:
an apnea-hypopnea event engine to detect, based on at least the sensed respiratory information, a number of apnea-hypopnea events, wherein the control portion is to automatically implement changes to the stimulation signal based upon changes in the detected number of apnea-hypopnea events.

22. The SDB care device of claim 21, wherein the control portion is to detect the number of apnea-hypopnea events according to the sensed respiratory information including at least one of changes in respiratory amplitude and changes in respiratory rate.

23. The SDB care device of claim 21, wherein the control portion is to determine, based on the sensed respiratory information, at least one of:
respiratory rate variability (RRV) information; and
respiratory rate information.

24. The SDB care device of claim 23, wherein the control portion is to determine sleep stage information based on the respiratory rate information and respiratory rate variability (RRV) information.

25. The SDB care device of claim 21, wherein the sensed respiratory information comprises at least one of:
respiratory period information; and
respiratory phase information.

* * * * *